(12) United States Patent
Lanning et al.

(10) Patent No.: US 8,738,139 B2
(45) Date of Patent: May 27, 2014

(54) WIRELESS SYSTEM FOR EPILEPSY MONITORING AND MEASUREMENT

(76) Inventors: Bruce Lanning, Littleton, CO (US);
James A. Nolan, Lakewood, CO (US);
Gregory J. Nuebel, Bailey, CO (US);
Dennis D. Spencer, Woodbridge, CT (US); Hitten P. Zaveri, New Haven, CT (US)

( * ) Notice: Subject to any disclaimer, the term of this patent is extended or adjusted under 35 U.S.C. 154(b) by 0 days.

(21) Appl. No.: 13/429,109

(22) Filed: Mar. 23, 2012

(65) Prior Publication Data

US 2012/0238855 A1  Sep. 20, 2012

Related U.S. Application Data

(63) Continuation of application No. 12/184,663, filed on Aug. 1, 2008, now Pat. No. 8,165,684.

(60) Provisional application No. 61/040,650, filed on Mar. 29, 2008, provisional application No. 60/963,012, filed on Aug. 1, 2007.

(51) Int. Cl.
*A61N 1/00* (2006.01)
*A61B 5/04* (2006.01)

(52) U.S. Cl.
USPC ............. 607/45; 607/33; 600/518; 600/544

(58) Field of Classification Search
USPC ............ 607/33, 45; 600/518, 544; 60/33, 45
See application file for complete search history.

(56) References Cited

U.S. PATENT DOCUMENTS

| | | | |
|---|---|---|---|
| 6,248,126 B1 | 6/2001 | Lesser et al. | |
| 6,549,804 B1 | 4/2003 | Osorio et al. | |
| 6,629,990 B2 | 10/2003 | Putz et al. | |
| 6,793,670 B2 | 9/2004 | Osorio et al. | |
| 6,882,881 B1 | 4/2005 | Lesser et al. | |
| 6,978,183 B2 | 12/2005 | Rothman | |
| 7,204,833 B1 | 4/2007 | Osorio et al. | |
| 7,212,851 B2 | 5/2007 | Donoghue et al. | |
| 7,228,171 B2 | 6/2007 | Lesser et al. | |
| 7,277,748 B2 | 10/2007 | Wingeier et al. | |
| 7,280,870 B2 | 10/2007 | Nurmikko et al. | |
| 7,313,440 B2 | 12/2007 | Miesel | |

(Continued)

OTHER PUBLICATIONS

Excerpts of International Search Report and Written Opinion for PCT/US08/009384. Date: Nov. 4, 2008. 4 pages.

(Continued)

*Primary Examiner* — Nicole F Lavert
(74) *Attorney, Agent, or Firm* — Welsh Flaxman & Gitler LLC

(57) ABSTRACT

A wireless system for brain monitoring/mapping of neurological-disorder patients includes a plurality of electrodes each configured for surface abutment of brain tissue and main circuitry for placement outside a body of a patient and configured to transmit power at radio frequencies and send and receive data using infrared energy. Remote circuitry is provided for subcutaneous implantation in a head of the patient. The remote circuitry is connected to the plurality of electrodes and includes a multiplexer sampling signals from the plurality of electrodes. The multiplexer outputs electrode signals to an amplifier and A/D converter for transmission to the main circuitry. The remote circuitry is configured to (a) receive transmitted power at radio frequencies from the main circuitry, (b) capture and digitize full-bandwidth EEG signals from each of the electrodes, and (c) send data to and receive data from the main circuitry using infrared energy.

22 Claims, 25 Drawing Sheets

(56) References Cited

U.S. PATENT DOCUMENTS

| | | | |
|---|---|---|---|
| 7,346,312 B2 | 3/2008 | Irazoqui-Pastor et al. | |
| 7,623,928 B2 | 11/2009 | DiLorenzo | |
| 7,917,206 B2 | 3/2011 | Frei et al. | |
| 8,135,473 B2 | 3/2012 | Miesel et al. | |
| 8,165,682 B2 | 4/2012 | Gopalsami et al. | |
| 8,332,024 B2 | 12/2012 | Rapoport et al. | |
| 8,353,837 B2 | 1/2013 | John et al. | |
| 8,380,314 B2 | 2/2013 | Panken et al. | |
| 2004/0054297 A1* | 3/2004 | Wingeier et al. | 600/544 |
| 2004/0133119 A1 | 7/2004 | Osorio et al. | |
| 2005/0215916 A1 | 9/2005 | Fadem et al. | |
| 2006/0173364 A1 | 8/2006 | Clancy et al. | |
| 2008/0077039 A1 | 3/2008 | Donnett et al. | |
| 2008/0208781 A1 | 8/2008 | Snyder | |
| 2008/0243022 A1 | 10/2008 | Donnett et al. | |
| 2009/0240314 A1 | 9/2009 | Kong et al. | |
| 2010/0106041 A1 | 4/2010 | Ghovanloo et al. | |
| 2011/0092842 A1 | 4/2011 | Decaria et al. | |
| 2012/0022391 A1 | 1/2012 | Leuthardt | |
| 2012/0116475 A1 | 5/2012 | Nelson et al. | |
| 2012/0123289 A1 | 5/2012 | Sorenson et al. | |
| 2012/0191157 A1 | 7/2012 | Stypulkowski et al. | |
| 2012/0203129 A1 | 8/2012 | Rennaker, II | |
| 2012/0209346 A1 | 8/2012 | Bikson et al. | |
| 2012/0271148 A1 | 10/2012 | Nelson | |
| 2012/0271189 A1 | 10/2012 | Nelson et al. | |
| 2012/0271374 A1 | 10/2012 | Nelson et al. | |
| 2012/0271375 A1 | 10/2012 | Wu et al. | |
| 2012/0277820 A1 | 11/2012 | Wu et al. | |
| 2012/0310298 A1 | 12/2012 | Besio et al. | |
| 2013/0138176 A1 | 5/2013 | Goetz | |

OTHER PUBLICATIONS

Chow, Eric Y., "High Data-Rate Wireless Transcutaneous-Telemetry Using High-Frequency Asics for Neural Prostheses." Thesis, Masters of Science in Electrical and Computer Engin.

Irazoqui-Pastor, Pedro, "Transcutaneous Inductively Powered Neural Recording System." Dissertation, Biomedical Engineering, University of California, Los Angeles, Ca. Date: 20.

Hassell, Travis, J. et al., "Constant-Current Adjustable Waveform Microstimulator for an Implantable Bi-Modal Output Hybrid Neural Prosthesis." Date: Apr. 2, 2007.

Moriziio, J. et al., "Wireless Headstage for Neural Prosthetics." Triangle BioSystems, Inc., Durham, NC. Date: Mar. 2005.

Chow, Eric Y., et al., Miniature Antenna for RF Telemetry through Ocular Tissue. Department of Electrical and Computer Engineering, Purdue University, West Lafayette, IN. Date.

Patterson, William R., et al. "A Microelectrode/Microelectronic Hybrid Device for Brain Implantable Neuroprosthesis Applications." IEEE Transactions on Biomedical Engineering.

Song, Yoon-Kyu et al., "Development of a Chipscale Integrated Microelectrode/Microelectronic Device for Brain Implantable Neuroengineering Applications." IEEE Transactions on.

Saito, Toshiyuki et al., "Radiotelemetry Recording of Electroencephalogram in Piglets During Rest." Physiology & Behavior, 84, pp. 725-731. Date: 2005.

Song, Yoon-Kyu et al., "A Brain Implantable Microsystem with Hybrid RF/IR Telemetry for Advanced Neuroengineering Applications." 29th Annual International Conference of the IE.

Yun, Xiao et al., "Low-Power High-Resolution 32-Channel Neural Recording System." 29th Annual Conference of the IEEE EMBS, Lyon, France. Date: Aug. 23-26, 2007.

Murari, Kartikeya et al., "Wireless Multichannel Integrated Potentiostat for Distributed Neurotransmitter Sensing." Engineering in Medicine and Biology 27th Annual Conference.

Farshchi, Shahin et al., "A TinyOS-Enabled MICA2-Based Wireless Neural Interface." IEEE Transactions on Biomedical Engineering, vol. 53, No. 7. Date: Jul. 2006.

Farshchi, Shahin et al., "Bi-Fi: An Embedded Sensor/System Architecture for Remote Biological Monitoring." IEEE Transactions on Information Technology in Biomedicine, vol. 11.

Borghi, T. et al., "A Compact Multichannel System for Acquisition and Processing of Neural Signals." 29th Annual Conference of the IEEE EMBS, Lyon, France. Date: Aug. 23-26, 2.

Chen, Hsin-Yung et al., "A Low Noise Remotely Controllable Wireless Telemetry System for Single-Unit Recording in Rats Navigating in a Vertical Maze." Med Biol Eng Comput, 46.

Mohseni, Pedram, Wireless Multichannel Biopotential Recording Using an . . . , IEEE Transactions on Neural Systems and Rehabilitation Engineering, Sep. 2005, 21(3): 263-271.

Chow, Eric Y., "High Data-Rate Wireless Transcutaneous-Telemetry Using High-Frequency Asics for Neural Prostheses." Thesis, Masters of Science in Electrical and Computer Engineering, Purdue University, West Lafayette, IN. Date: May 2007.

Irazoqui-Pastor, Pedro, "Transcutaneous Inductively Powered Neural Recording System." Dissertation, Biomedical Engineering, University of California, Los Angeles, CA. Date: 2003.

Chow, Eric Y., et al., Miniature Antenna for RF Telemetry through Ocular Tissue. Department of Electrical and Computer Engineering, Purdue University, West Lafayette, IN. Date: Copyright 2008.

Patterson, William R., et al. "A Microelectrode/Microelectronic Hybrid Device for Brain Implantable Neuroprosthesis Applications." IEEE Transactions on Biomedical Engineering, No. 10, vol. 51. Date: Oct. 2004.

Song, Yoon-Kyu et al., "Development of a Chipscale Integrated Microelectrode/Microelectronic Device for Brain Implantable Neuroengineering Applications." IEEE Transactions on Neural Systems and rehabilitation Engineering, vol. 13, No. 2. Date: Jun. 2005.

Song, Yoon-Kyu et al., "A Brain Implantable Microsystem with Hybrid RF/IR Telemetry for Advanced Neuroengineering Applications." 29th Annual International Conference of the IEEE Embs, Lyon, France. Date: Aug. 23-26, 2007.

Murari, Kartikeya et al., "Wireless Multichannel Integrated Potentiostat for Distributed Neurotransmitter Sensing." Engineering in Medicine and Biology 27th Annual Conference, Shanghai, China. Date: Sep. 1-4, 2005.

Farshchi, Shahin et al., "Bi-Fi: An Embedded Sensor/System Architecture for Remote Biological Monitoring." IEEE Transactions on Information Technology in Biomedicine. vol. 11, No. 6. Date: Nov. 2007.

Borghi, T. et al., "A Compact Multichannel System for Acquisition and Processing of Neural Signals." 29th Annual Conference of the IEEE EMBS, Lyon, France. Date: Aug. 23-26, 2007.

Chen, Hsin-Yung et al., "A Low Noise Remotely Controllable Wireless Telemetry System for Single-Unit Recording in Rats Navigating in a Vertical Maze." Med Biol Eng Comput, 46:833-839. Date: 2008.

\* cited by examiner

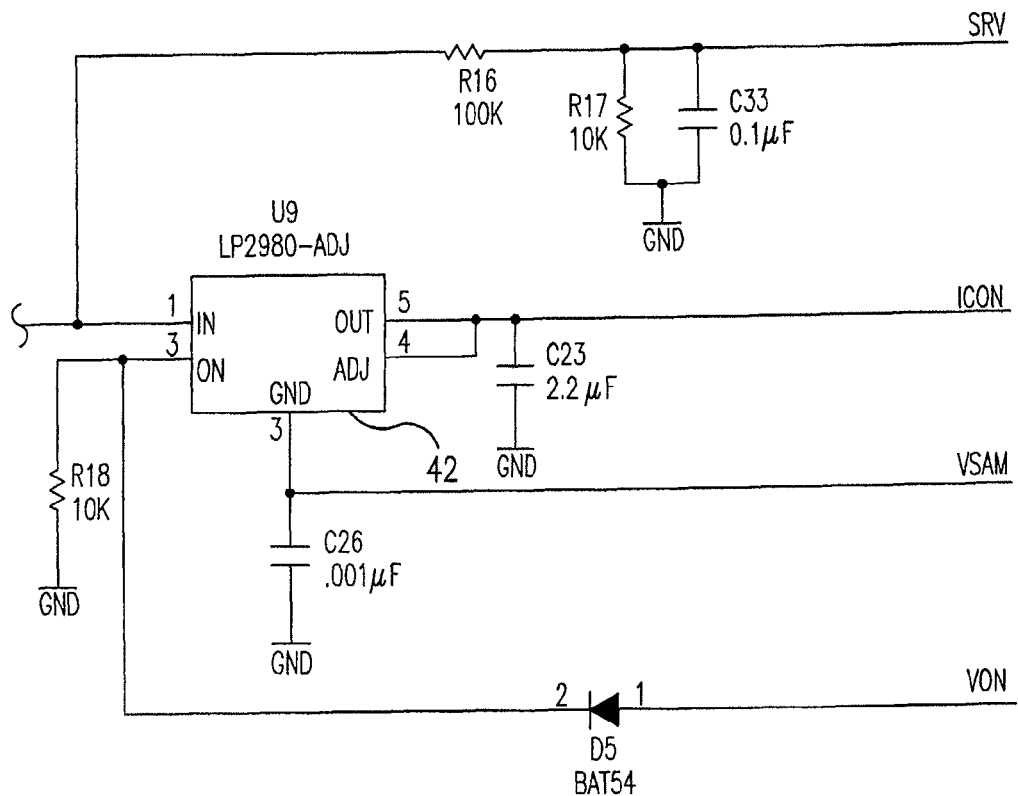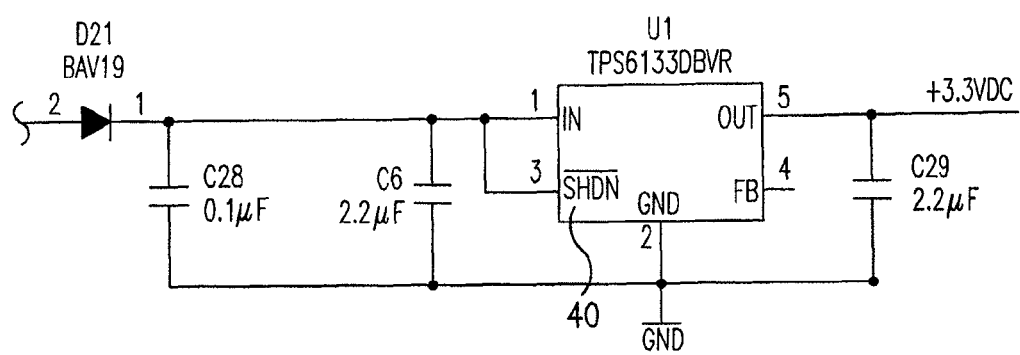
FIG. 10B

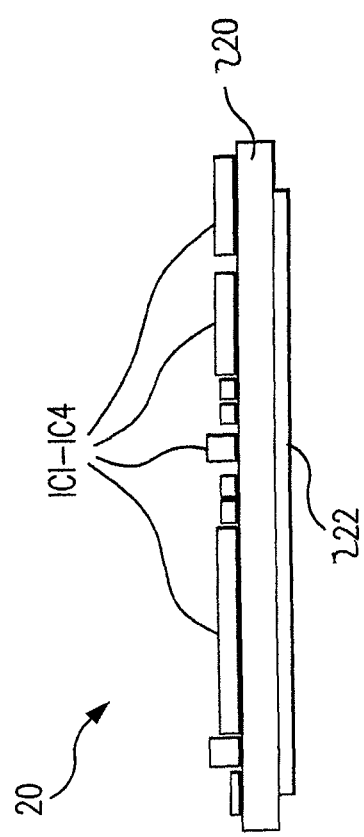

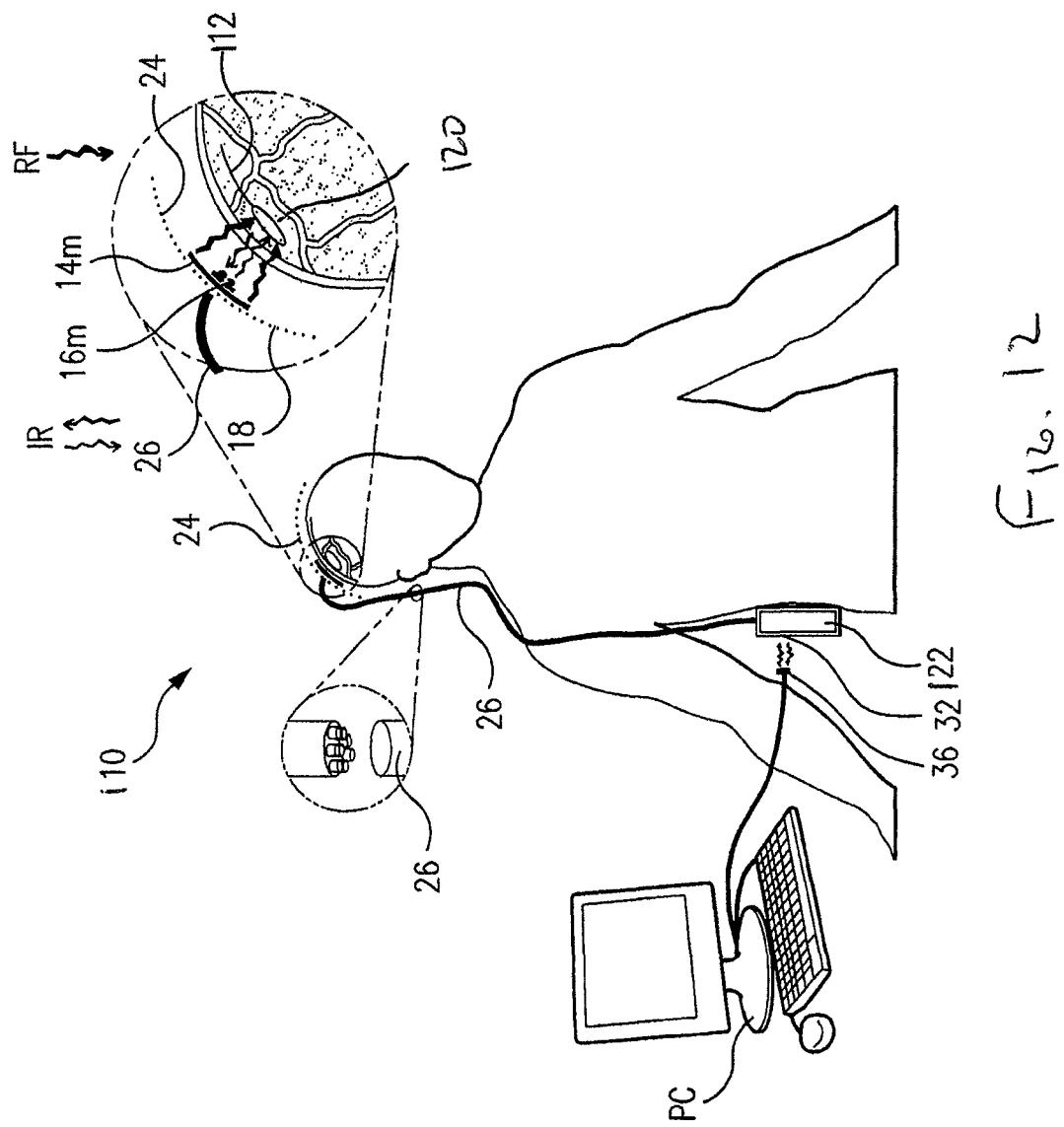

WIRELESS SYSTEM FOR EPILEPSY MONITORING AND MEASUREMENT

CROSS REFERENCE TO RELATED APPLICATIONS

This application is a continuation in part of U.S. patent application Ser. No. 12/184,663, filed Aug. 1, 2008, entitled "WIRELESS SYSTEM FOR EPILEPSY MONITORING AND MEASUREMENT", which is now U.S. Pat. No. 8,165,684 issued on Apr. 24, 2012, which claims benefit of U.S. Provisional Patent Application Ser. No. 61/040,650, filed Mar. 29, 2008, and U.S. Provisional Patent Application Ser. No. 60/963,012, filed Aug. 1, 2007, the entire contents of which are incorporated herein by reference.

FIELD OF THE INVENTION

The invention relates generally to devices for monitoring of brain activity and mapping brain function in epilepsy patients and patients with other neurological disorders and, more particularly, to systems which facilitate accurate measurement for periods of time through the use of implanted devices and electrodes.

BACKGROUND OF THE INVENTION

Accurate sensing of intracranial electrical activity, such as for determining epileptogenic foci, mapping brain function or otherwise, often may require use of a plurality of brain contacts. Epileptogenic mapping is one example of the use of electrical devices with tissue-engagement contacts. Examples of two kinds of intracranial electrical contact devices are depth probes and flexible flat surface members.

Depth probes, which may be referred to as "depth electrodes", penetrate deep into the brain tissue. On the other hand, flexible flat surface members, including what are sometimes referred to as "strip" electrodes and "grid" electrodes, may be placed subdurally in direct contact with brain tissue at the surface of the brain.

Examples of such electrodes include but are not limited to electrodes described in U.S. Pat. No. 4,735,208 (Wyler et al.), U.S. Pat. No. 4,805,625 (Putz), U.S. Pat. No. 4,903,702 (Putz), U.S. Pat. No. 5,044,368 (Putz) and U.S. Pat. No. 5,097,835 (Putz).

Each of these different kinds of intracranial tissue-engagement electrodes is connected to some circuitry which typically captures and records the EEG (electroencephalography) signals for analysis of various types. There is a diagnostic need for an increased number of electrodes in order to increase the precision of analysis and diagnosis based on the captured EEG information. An increase in the number of electrodes requires higher data transmission bandwidths if the full amount of data captured from the electrodes is delivered to the monitoring system electronics. Further, there is a diagnostic need to monitor patients for longer periods of time, again for increased precision of diagnosis.

State-of-the-art monitoring systems in diagnostic use, or at least the great majority of such systems, today require a patient suffering from epilepsy to have at least one opening through the patient's skin during the entire period in which the electrodes are implanted for monitoring purposes. It is highly desirable medically, however, to avoid wires/devices through the skin to be in place during such monitoring, since any opening in the skin is an opportunity for infection to develop. Thus, it is highly desirable to avoid prolonged periods during which there are openings in the skin. Further, monitoring systems typically require that a patient be tethered by wires to the monitoring equipment. The existence of a tether is both interfering and inconvenient.

Monitoring systems with electrodes placed to abut brain tissue in various configurations can also be used to provide electrical stimulation of brain tissue as one mode of medical treatment. In making EEG measurements or delivering such electrical stimulation, there is a need to know over time what the condition of an implanted electrode is while it abuts brain tissue. An electrode may shift from its initial implanted position or lesions may form at an electrode, thereby changing conditions under which monitoring and/or stimulation occur in a way which affects the degree of precision of such monitoring and/or stimulation. Knowing and reacting to the electrical impedance of implanted electrodes and to impedance changes would be important to assessment of the condition of an implanted electrode and to enhancing the precision of diagnosis and treatment. One aspect of the present invention provides such impedance-measuring capability.

In order to meet some of the above-mentioned needs, in particular the need to avoid openings in the skin for prolonged periods of time, it is desirable to implant not only the electrodes but also the circuitry which interfaces the electrodes with the remainder of the monitoring system. In order to accomplish this, power must be provided to such an implanted device. This creates a need for low power consumption and medically-safe approaches to providing power.

Power can be provided to an implanted device by either providing an onboard source of power such as a battery or by transmitting power to the implanted device. In the case of devices to which power is transmitted, there is a need to transmit power with as low power loss as possible in order to affect human tissue as little as possible. In the case of providing onboard power, there is a need for completely dry and fully-encased power sources.

Some wireless brain-interactive systems have previously been disclosed in the literature for various purposes, including for monitoring EEG signals in patients. Prior wireless systems for monitoring EEG signals in patients fall short of meeting the wide variety of needs which characterize the complex challenges facing the medical community in providing such diagnosis and treatment today.

Certain other wireless brain-interactive systems in the literature are directed toward providing a brain-machine interface to allow amputees to control prosthetic limbs, an entirely different application than brain monitoring/mapping of neurological-disorder patients. Unlike monitoring/mapping systems, which seek to capture signals that are composites of the signals from a great many neurons, brain-machine interface systems are typically concerned with capturing signals from individual neurons. Significant differences exist in the nature of the electrodes of these two sorts of systems, as does the type of processing that would be required and the bandwidths involved. With regard to the electrodes, brain-machine interface systems have point-like brain-tissue contact, while monitoring/mapping systems employ surface contact, either involving flat disk surfaces or cylindrical surfaces. The present invention is in the specific field of monitoring/mapping systems. The solutions used in brain-machine interface are also more concerned with detecting a time-stamp of activity and transmitting this time-stamp rather than the continuously varying brain signal.

The wireless system for monitoring/mapping brain tissue disclosed herein meets the complex set of needs in the monitoring/mapping field. Among the needs addressed are the need for an increased number of electrodes with all of the data available in the EEG signal at each electrode being captured with high precision in real-time and available for analysis, and the need to assess the condition of the implanted electrodes over time to assure proper capturing of EEG signals on the surface electrodes used.

OBJECTS OF THE INVENTION

It is an object of the invention, in the field of EEG monitoring, to provide a monitoring system which overcomes certain problems of the prior art, including those mentioned above.

Another object of the invention is to provide an improved system for monitoring brain tissue which eliminates openings in the skin for prolonged periods.

Another object of the invention is to provide an improved wireless system for monitoring brain tissue which enables the monitoring of a large number of implanted electrodes in order to increase the precision of the diagnostic information produced, thereby improving diagnostic accuracy.

Still another object of the invention is to provide an improved wireless system for monitoring brain tissue which captures and transmits the full amount of information contained in the EEG signals.

Yet another object of the invention is to provide an improved wireless system for monitoring brain tissue which consumes low power and thus generates low heat and can be physically small, thereby avoiding a large implanted device.

Another object of the invention is to provide an improved system for monitoring brain tissue without a tether to the patient.

Another object of the invention is to provide an improved wireless system for monitoring brain tissue which may operate without an implanted battery.

Another object of the invention is to provide an improved wireless system for monitoring brain tissue which may include a medically-safe battery for certain periods of operation.

Yet another object of the invention is to provide an improved wireless system for monitoring brain tissue which provides increased freedom for the monitored patient.

Still another object of the invention is to provide an improved wireless system for monitoring brain tissue which has low power losses within the skin tissue surrounding the implanted device.

Another object of the invention is to provide an improved system for monitoring brain tissue which provides measurements of implanted electrode electrical impedance in order to assess the condition of electrodes over time.

Another object of the invention is to provide an improved system for monitoring brain tissue which can be retained within a patient during an MRI procedure.

It is also an object of the present invention to provide a wireless system for brain monitoring/mapping of neurological-disorder patients. The system includes a plurality of electrodes each configured for surface abutment of brain tissue. The system also includes main circuitry for placement outside a body of a patient and configured to transmit power at radio frequencies and send and receive data using infrared energy. Remote circuitry for subcutaneous implantation in a head of the patient is also provided. The remote circuitry is connected to the plurality of electrodes and includes a multiplexer sampling signals from the plurality of electrodes, the multiplexer outputting electrode signals to an amplifier and A/D converter for transmission to the main circuitry. The remote circuitry is configured to (a) receive transmitted power at radio frequencies from the main circuitry, (b) capture and digitize full-bandwidth EEG signals from each of the electrodes, and (c) send data to and receive data from the main circuitry using infrared energy, including sending the digitized full-bandwidth EEG signals from each of the electrodes.

It is a further object of the present invention to provide a signal processing circuitry for brain monitoring/mapping of neurological-disorder patients. The signal processing circuitry includes a plurality of electrodes and a multiplexer sampling signals from the plurality of electrodes. The multiplexer outputs electrode signals to an amplifier receiving electrode signals output by the multiplexer. The circuitry also includes an A/D converter receiving amplified signals from the amplifier for transmission to an EEG recording device.

These and other objects of the invention will be apparent from the following descriptions and from the drawings.

SUMMARY OF THE INVENTION

The present invention is a wireless system for monitoring the brain tissue of a patient. The system comprises (1) a plurality of electrodes configured to abut brain tissue, (2) main circuitry for placement outside the body of the patient and configured to transmit power at radio frequencies and send and receive data using infrared energy, and (3) remote circuitry for subcutaneous implantation in the head of a patient, the remote circuitry being connected to the plurality of electrodes and configured to (a) receive transmitted power at radio frequencies from the main circuitry, (b) capture and digitize EEG signals from each of the electrodes, and (c) send data to and receive data from the main circuitry using infrared energy, including sending the digitized EEG signals from each of the electrodes sampled to capture the full bandwidth of each EEG signal.

In some preferred embodiments of the invention, the radio frequencies are in the range of between 13.55 MHz and 13.57 MHz. Also in some embodiments, each digital signal has a digital resolution of at least about 12-16 bits, and it is contemplated the A/D resolution will be improved to 22 or 24 bits. In highly-preferred embodiments, the sampling frequency is currently close to 1000 Hz.

In some preferred embodiments of the inventive wireless brain-monitoring system, the remote circuitry is further configured to measure the electrical impedance of each of the plurality of electrodes. Further, in some embodiments, the remote circuitry is further configured to send the impedance measurements to the main circuitry as digital signals.

Some embodiments of the inventive brain-monitoring system include a power storage capacitor in the remote circuitry to provide power when high current flow is required.

Further, some preferred embodiments of the brain-monitoring system include a battery as part of the remote circuitry to augment the RF-supplied power. In some highly-preferred embodiments, the battery is a solid-state lithium rechargeable battery.

In other preferred embodiments of the inventive wireless brain-monitoring system, the remote circuitry further includes at least one circuit-loop-interrupting element having an open state, thereby rendering the remote circuit MRI-safe when the at least one circuit-loop-interrupting element is in the open state.

Some other embodiments of the inventive system include a video camera and recording system to simultaneously record the EEG signals and video images of the patient.

Further, some preferred embodiments of the inventive system for monitoring the brain tissue of a patient are not wireless systems and comprise a plurality of electrodes configured to abut brain tissue and circuitry connected to the plurality of electrodes and configured to (a) capture EEG signals from the electrodes and (b) measure the electrical impedance of each of the plurality of electrodes, thereby to monitor the condition of the electrode/tissue interfaces to enable interpretation of captured EEG signals. Some of these preferred embodiments are further configured to provide electrical energy to at least one of the plurality of electrodes to stimulate brain tissue.

Other embodiments of the present invention provide for a wireless system for brain monitoring/mapping of neurological-disorder patients including remote circuitry connected to the plurality of electrodes and a multiplexer sampling signals from the plurality of electrodes, the multiplexer outputting electrode signals to an amplifier and A/D converter for transmission to the main circuitry. The remote circuitry is configured to (a) receive transmitted power at radio frequencies from the main circuitry, (b) capture and digitize full-bandwidth EEG signals from each of the electrodes, and (c) send data to and receive data from the main circuitry using infrared energy, including sending the digitized full-bandwidth EEG signals from each of the electrodes.

The present invention also provides for signal processing circuitry for brain monitoring/mapping of neurological-disorder patients. The signal processing circuitry includes a plurality of electrodes and a multiplexer sampling signals from the plurality of electrodes. The multiplexer outputs electrode signals to an amplifier receiving electrode signals output by the multiplexer. The circuitry also includes an A/D converter receiving amplified signals from the amplifier for transmission to an EEG recording device.

As used herein, the term "full bandwidth" means having a bandwidth which is wide enough to include the data contained in each of the monitored EEG electrodes, the data content including information at all frequencies up to, for example, at least 250 Hz or higher. When an analog signal contains frequencies up to a frequency $f_1$ cycles per second and such a signal is sampled to create a stream of digital signals, information theory requires that the sampling rate be at least $2 \cdot f_1$ times per second in order to retain all of the data contained in the analog signal. Further, if there are N such analog signals being sampled from, say, N electrodes, and each of such digital signals is represented by a digital signal using D bits per sample, then the minimum amount of data in a combined digital signal having "full bandwidth" is equal to $2 \cdot f_1 \cdot N \cdot D$ bits per second, assuming no extra bits of information are included in the signal. For example, the minimum "full bandwidth" of a combined digital signal in a system which has 256 electrodes and 16 bits per sample, sampled at 500 Hz is just over 2 Mbits per second.

As used herein, the word "abut" pertaining to the position of an electrode with respect to brain tissue refers to an electrode coming in contact with the brain tissue in any way, including being placed next to the tissue and being positioned to penetrate the tissue.

As used herein, the term "circuit-loop-interrupting element" means a device which breaks a circuit loop or places a suitably high impedance within a circuit loop such that little or no current will be induced to flow in such loop during exposure to an MM operating environment.

The term "MRI-safe" as used herein means a device is configured to be present in an MRI operating environment (with the device not operating) without either damage occurring to the device or the tissue of the patient whose head contains the device. For example, a number of steps can be taken to render an electrical device MRI-safe. MM-safe in the context of this document indicates that the step being indicated contributes to the MM safety of the circuit, not that it alone renders the entire device MRI-safe.

BRIEF DESCRIPTION OF THE DRAWINGS

The drawings illustrate preferred embodiments which include the above-noted characteristics and features of the invention. The invention will be readily understood from the descriptions and drawings.

FIG. 9A also illustrates an infrared data link to a computer which communicates with the main circuitry over such a data link.

FIG. 11 is a schematic illustration of the inclusion of a solid-state lithium rechargeable battery in the packaging of the alternative embodiment of the remote circuitry of the inventive brain-monitoring system as shown in FIG. 10.

FIGS. 12, 13 and 14 are various drawings disclosing an alternate embodiment in accordance with the present invention.

DETAILED DESCRIPTION OF PREFERRED EMBODIMENTS

The implantable wireless EEG system measures brainwave signals and transmits them via an infrared signal through the skin/bone to an external infrared receiver for analysis. The implantable wireless EEG system can be powered by an external RF field, powered internally by a battery and have the battery charged by an external field. The implantable system is completely sealed within the body, usually in a cavity cut out in the skull. When the implantable wireless EEG system is powered by an external RF field the implanted system is electrically active only when external RF power is turned on and completely passive otherwise; it does not have any active electrical components when it is not being used.

Figure 13:
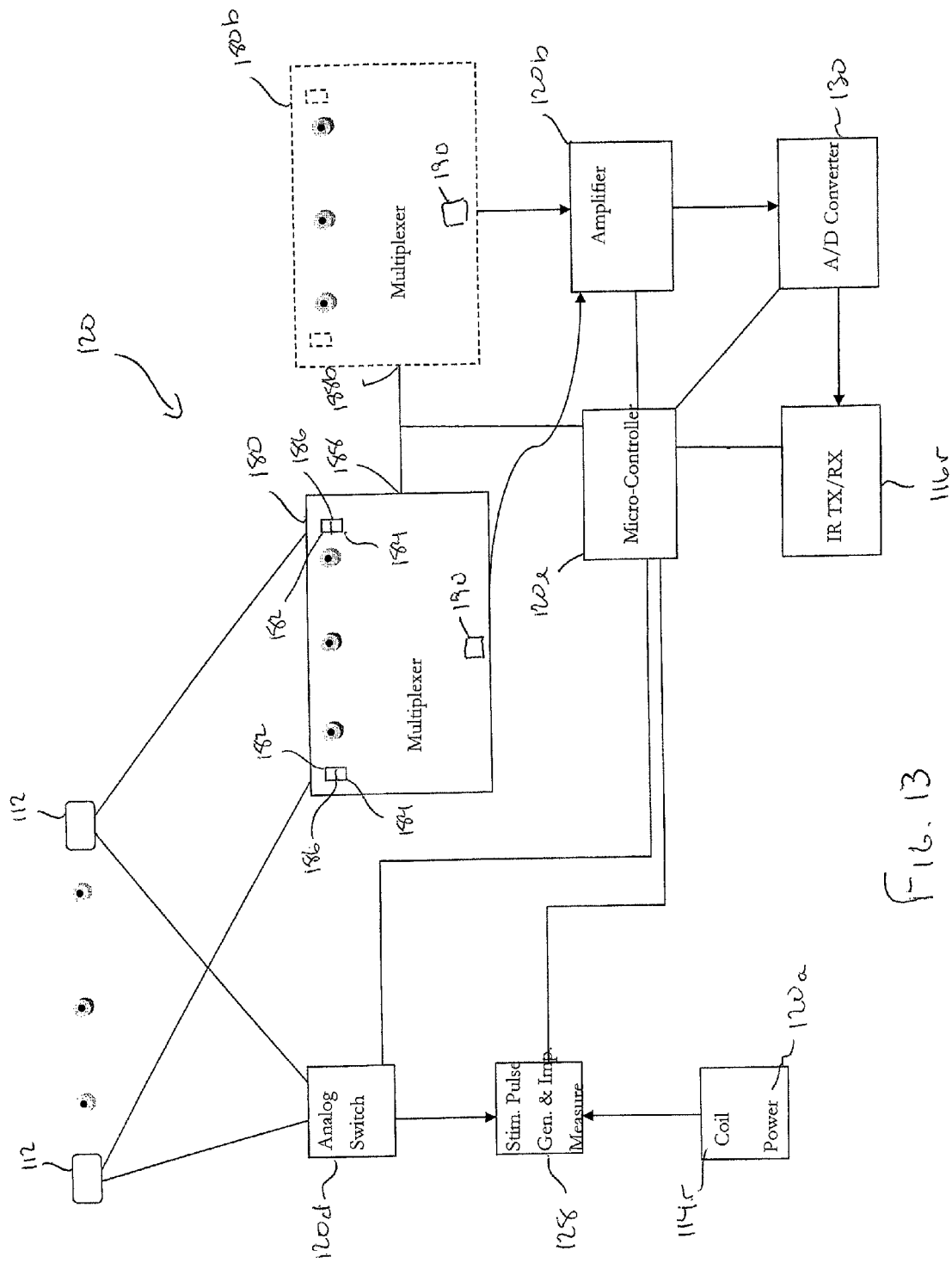
Figure 14:
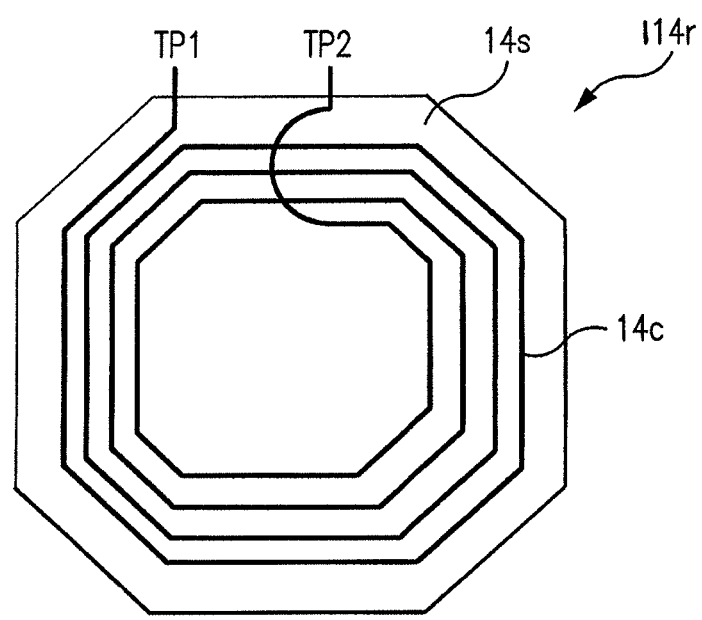

As will be appreciated based upon the following disclosure, an alternative embodiment of the present implantable wireless EEG system as disclosed with reference to FIGS. 12, 13 and 14, which permits the connection of the implantable system to the external system through a much reduced set of wires to transmit power and digital data. In accordance with the embodiment disclosed with reference to FIGS. 1 to 11, a single wire is used to transmit the analog signal from each electrode. The embodiment of FIGS. 12, 13 and 14 allows for the use of a small set of wires to transmit power to the implantable system and data from all electrodes in a single digital data stream.

The components of the system are electrodes, multiplexer, amplifier, A/D converter, microprocessor, infrared transceiver, antenna, power supply, external receiver, and external power transmitter. The electrodes are distributed over the brain surface and/or inserted into the brain. These electrodes are then connected to a multiplexer that selects the appropriate electrode to be measured. The multiplexer is controlled by the microprocessor. The selected electrode or "channel" is then amplified by an amplifier which feeds the signal into an A/D converter. The A/D converter is controlled by the microprocessor which reads the data and sends it to an infrared transceiver which then sends an infrared signal through the skull and/or tissue to an external receiver. The power supply picks up an external RF signal via the antenna, rectifies it and uses the rectified voltage to power the implant. The rectified voltage is regulated with a voltage regulator integrated circuit.

Figure 1:
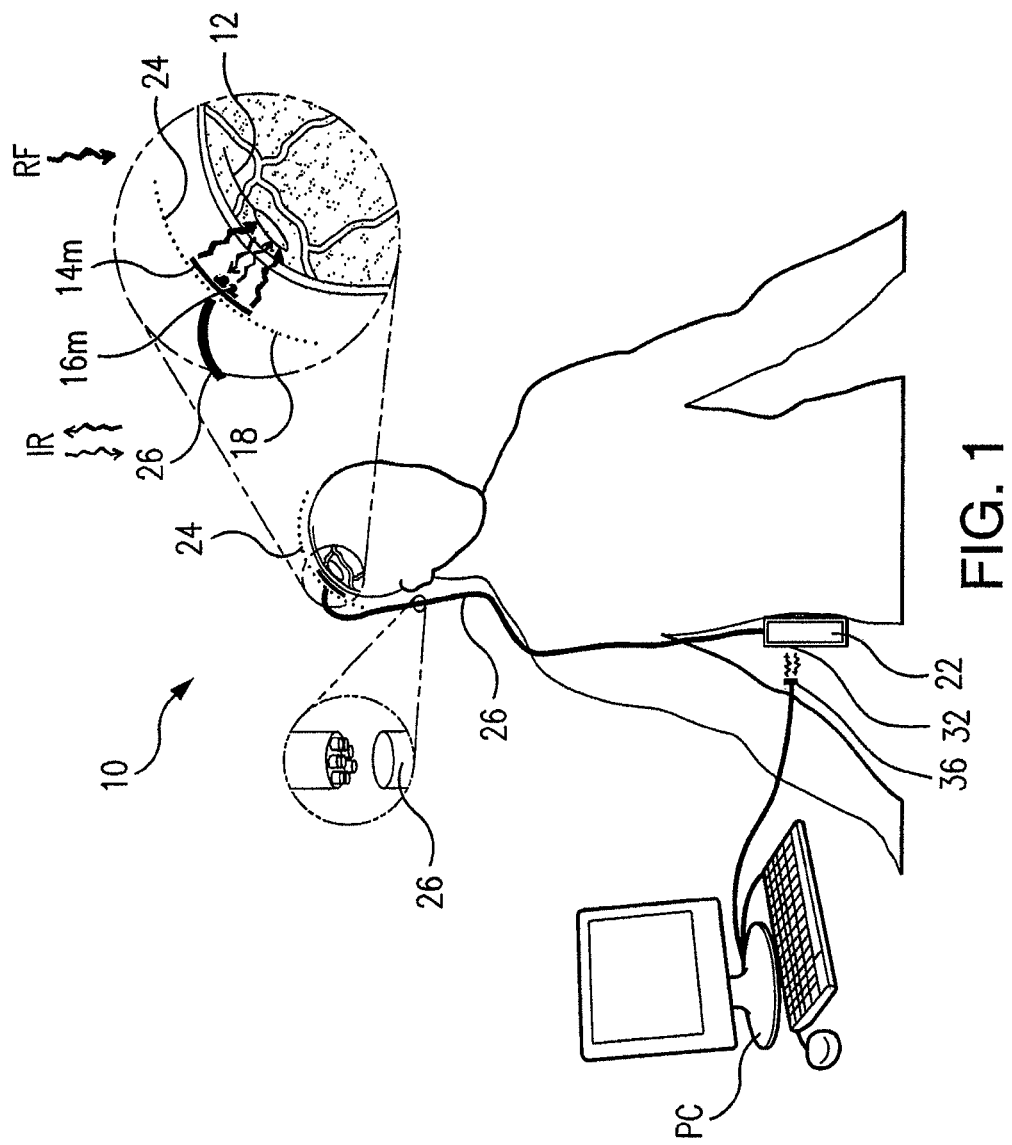
FIG. 1 is a schematic diagram of one embodiment of the inventive wireless system for monitoring the brain tissue of a patient.

FIG. 1 is a schematic diagram of one embodiment of the inventive wireless system for monitoring the brain tissue of a patient. A plurality of electrodes 12 are implanted in the human brain to abut brain tissue, and are positioned to monitor EEG signals where the physician performing the procedure determines are regions of interest within the patient's brain. (In this document, reference number 12 is used when referring to either a single selected electrode or the plurality of electrodes. In each case, the single/plural context is clear.) Electrodes 12 are connected to an implanted device containing remote circuitry 20. Included as part of remote circuitry 20 is an RF inductive receive coil 14r connected to TP1 and TP2 in FIGS. 4 and 10. One embodiment of coil inductive receive coil 14r is shown in FIG. 4A. Also included in remote circuitry 20 is an infrared transceiver 16r (shown in FIG. 6) for transmitting and receiving data with an infrared signal across the skin 18 of the patient being monitored. IR transceiver 16r is aligned with a hole in the patient's skull in order to transmit and receive IR signals through skin 18.

Figure 9:
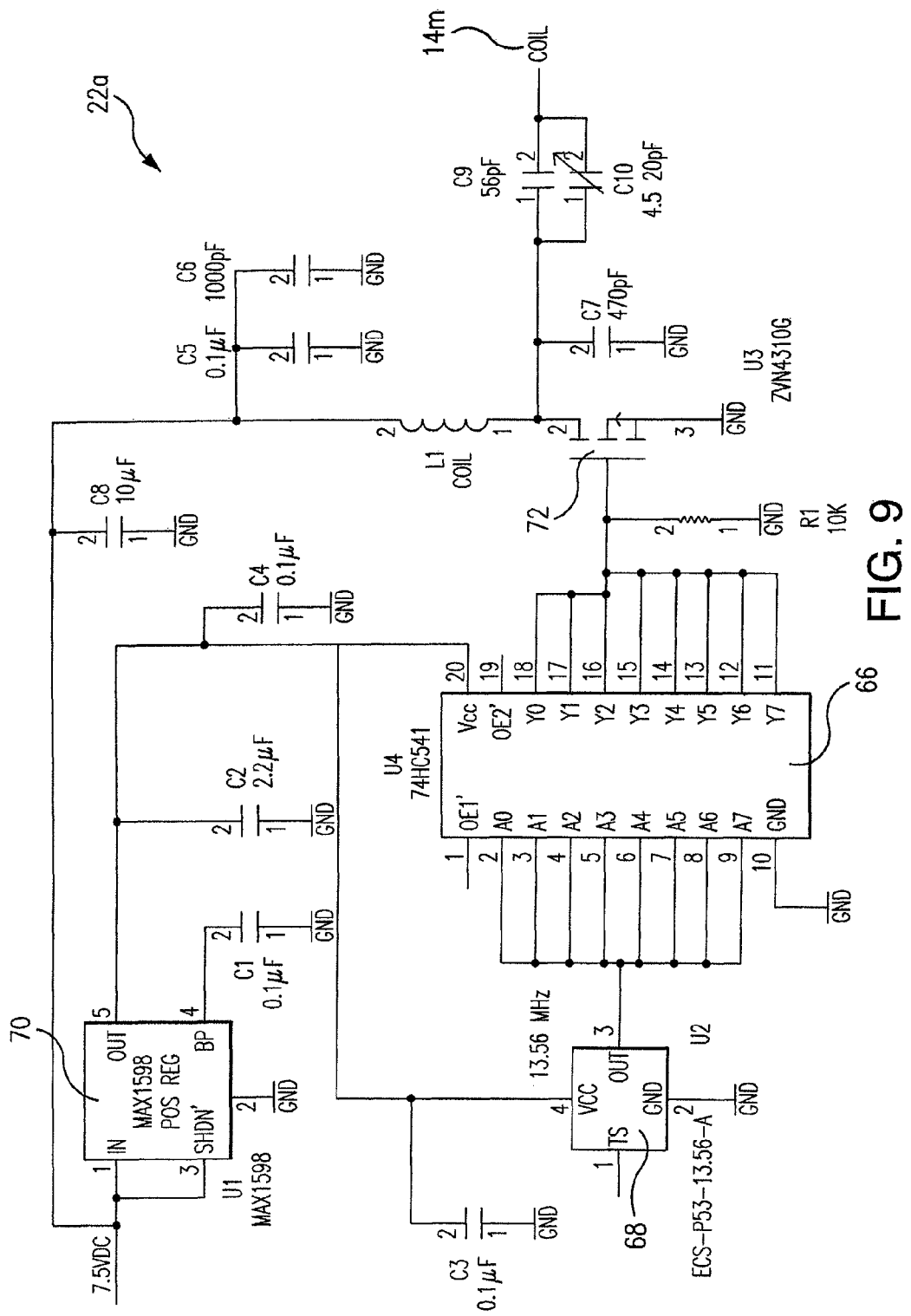
FIG. 9 is a circuit diagram of a portion of the main circuitry of the inventive brain-monitoring system of FIG. 1, illustrating an embodiment of the RF power amplifier therein.

Wireless monitoring system 10 also includes main circuitry 22 (also shown in FIG. 9). Main circuitry 22 includes an RF inductive transmit coil 14m to transmit power to remote circuitry 20 and an IR transceiver 16m to receive data from and send data to remote circuitry 20. Both inductive transmit coil 14m and transceiver 16m are located at the end of suitable cabling 26 to main circuitry 22 such that these elements can be conveniently positioned with respect to the head of the patient being monitored.

RF inductive receive coil 14r within remote circuitry 20 receives power from an RF inductive transmit coil 14m which is part of main circuitry 22. FIG. 1 shows one embodiment of how inductive transmit coil 14m may be positioned to transmit power to remote circuitry 20 through skin 18, using a flexible cap 24 to hold inductive transmit coil 14m and IR transceiver 16m in place.

As shown in FIG. 1, main circuitry 22 may be interfaced with a computer (labeled PC) through the use of an IR transceiver 32 connected to a serial port on main circuitry 22. IR transceiver 32 communicates with a similar dongle 36 connected with a serial port on the computer (PC). Such IR transceiver dongle devices are well-known to those skilled in the art, and further details are not included in this document on IR transceiver 36. There are other ways in which data received from remote circuitry 20 can be handled and the embodiments shown herein are not intended to be limiting in any way.

Figure 2:
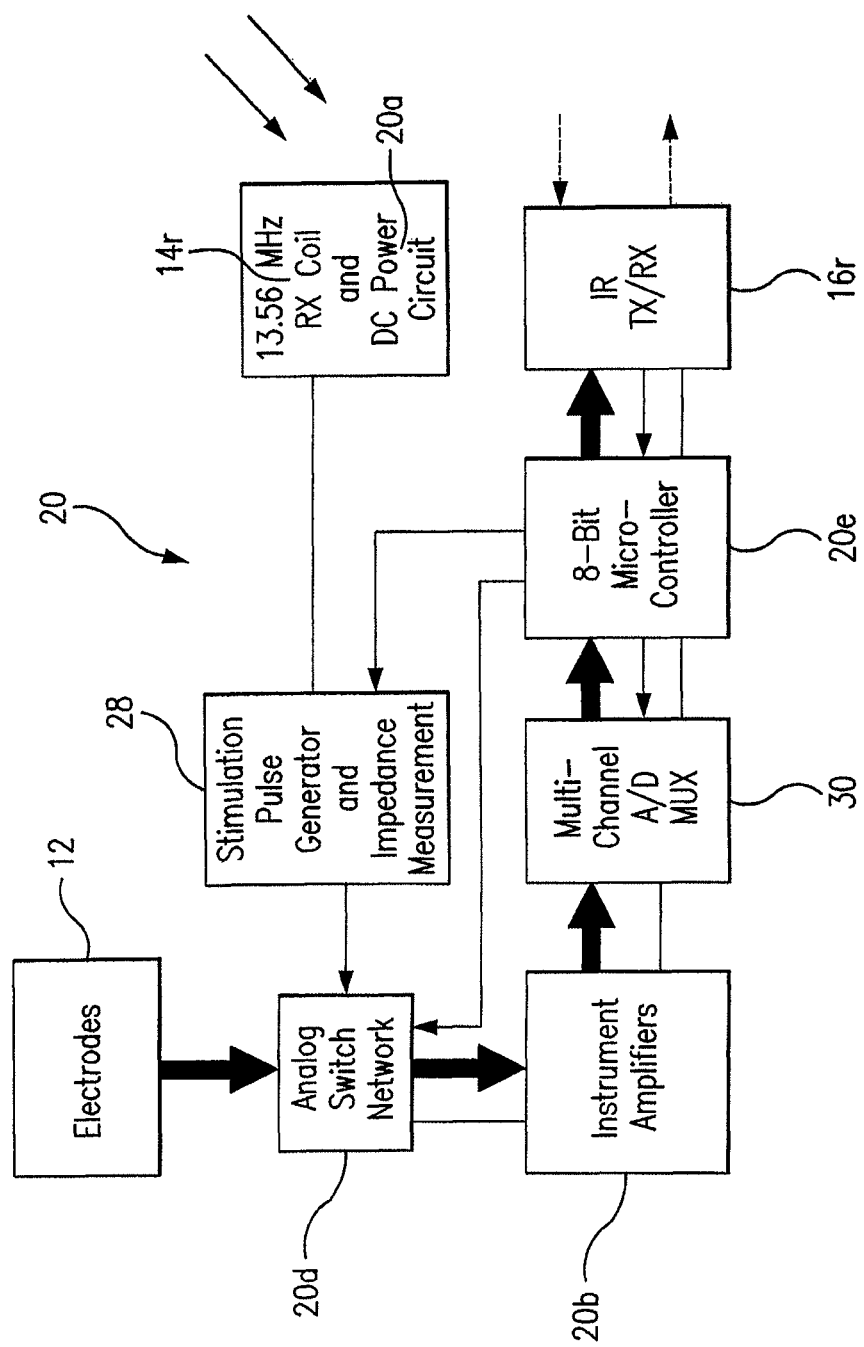
FIG. 2 is a functional block diagram of the remote circuitry and electrodes of the inventive brain-monitoring system of FIG. 1.

FIG. 2 is a functional block diagram of remote circuitry 20 and electrodes 12 of the inventive brain-monitoring system of FIG. 1. FIG. 2 illustrates the interconnectivity among the various portions of remote circuitry 20. The functional blocks in FIG. 2 are labeled, as appropriate, with reference numbers which correspond to the primary portions of remote circuitry 20 as illustrated in FIGS. 4 through 8. Electrodes 12 are connected by an analog switch network 20d (detailed in FIG. 7). Analog switch network 20d creates connections between individual electrodes and functional circuitry 28 which provides tissue stimulation current and which enables remote circuitry 20 to measure electrode impedance (detailed in FIG. 7).

An array of instrument amplifiers 20b (detailed in FIG. 5) condition the EEG signals from electrodes 12 and connect to an analog-to-digital (A/D) converter 30 which transforms the multiple analog EEG signals to digital signals in a multiplexed fashion. Under the control of a micro-controller 20e, these digital signals are transmitted to main circuitry 22 via IR transceiver 16r. Micro-controller 20e, with programmed instructions in firmware stored within micro-controller 20e, controls the functions of remote circuitry 20 and communicates with main circuitry 22.

DC power circuitry 20a to which RF inductive receive coil 14r is connected is also included in remote circuitry 20. Power circuit 20a receives transmitted power at RF frequencies from main circuitry 22 in order to power all of the elements of remote circuitry 20.

Figure 3:
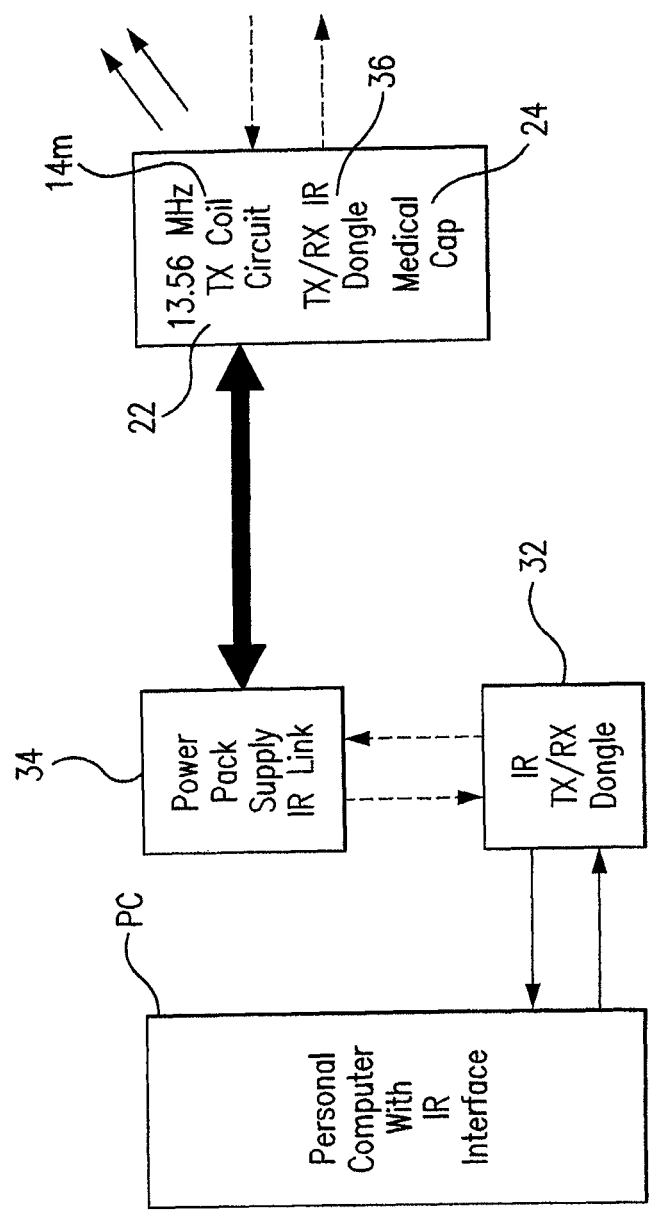
FIG. 3 is a functional block diagram including the main circuitry of the inventive brain-monitoring system of FIG. 1.

FIG. 3 is a functional block diagram including main circuitry 22 of inventive brain-monitoring system 10 of FIG. 1. Also functionally illustrated in FIG. 3 are a computer (PC) which communicates with main circuitry 22 through an IR transceiver dongle 32 which is used to communicate between the computer (PC) and main circuitry 22 when monitoring system 10 is operated without a tether. As stated above, such IR transceiver dongle devices are well-known to those skilled in the art of circuit design. An IR transceiver dongle 36 is connected to a serial port on the computer (PC) to complete the IR data link between main circuitry 22 and the computer (PC). Although IR transceivers 32 and 36 are illustrated as being positioned close to each other, there is no such limitation in the physical arrangement. IR transceivers 32 and 36 may be devices which have a range much longer than that shown in FIG. 3, thereby removing the inconvenience and interference of a tether to the computer (PC). Alternative wired and wireless transmission schemes can also be used to communicate between the PC and the main circuitry 22.

Alternatively, it is also possible to integrate digital data recording capability within the main circuitry 22 in the form of a buffered memory which can then be transmitted to the PC when the PC and main circuitry 22 are connected.

As stated above, details of the circuitry used to complete the data link to the computer (PC) using standard formats and protocols are well-known by those skilled in the art of circuit design and digital design and thus are not included herein. FIG. 3 also includes a functional block 34 which is a standard power supply for main circuitry 22.

FIGS. 4 and 5 through 8 are circuit diagrams of the embodiment illustrated and described generally in FIGS. 1-3. Each of these figures shows a portion of remote circuitry 20 within an embodiment of inventive brain-monitoring system 10. The portions of remote circuitry 20 are interconnected as labeled in the figures, according to standard practice within the field of circuit design, illustrating the various points at which the portions of remote circuitry 20 are joined.

Remote circuitry 20 as shown in these figures has an arbitrary number (n) of electrodes, and remote circuitry 20 is shown as being expandable to provide the configuration necessary to monitor such an arbitrary number of electrodes. Larger numbers of electrodes provide greater precision in sensing certain intracranial electrical activity such as the location of epileptogenic foci to create an epileptogenic map for patient diagnosis. Many parts of remote circuitry 20 can be replicated as the number (n) of electrodes is increased, and FIGS. 5 through 8 illustrate such scaling of remote circuitry 20. For example, there is an instrument amplifier required for each of the n electrodes. In a similar fashion, depending on the number of A/D channels, switches, I/O lines, etc. in various integrated circuits, the number of such circuits required will vary depending on the value of n. Such a general situation is illustrated by the scalable portions of the circuitry in FIGS. 5 through 8. Such replication and scaling is well-known to those skilled in the art of circuit design and digital design.

In this embodiment of monitoring system 10, RF power is transmitted from main circuitry 22 to remote circuitry 20 preferably at a frequency of 13.56 MHz. This frequency is particularly well-suited to such an application since, as an FCC-designate ISM band set aside for industrial, scientific and medical devices, the band of 13.553 to 13.567 MHz (centered on 13.560 MHz) is the ISM band which has the lowest loss and least heating of body tissue. (See the Handbook of Biological Effects of Electromagnetic Fields by Polk and Postow, CRC Press, p. 88-91, 1991.) Biological tissue at 13.56 MHz has the lowest conductivity which means that the RF signal will penetrate the tissue to the greatest depth at this frequency.

At a frequency of 13.56 MHz, inductive receive and transmit coils such as 14r and 14m primarily create a magnetic field confined to the locality around the coil. The field diminishes rapidly with distance from the coil, much more rapidly than an electric field under the same circumstances. Thus, the fields which couple the coils are the near fields of the coil. The near field contains the propagating field, the energy storing both the electric and magnetic fields. In the near field, there is much more energy per unit volume available than in the far field; therefore, a higher degree of coupling can be achieved than in the far field alone, thereby increasing the energy transfer efficiency of the circuits.

Figure 4:
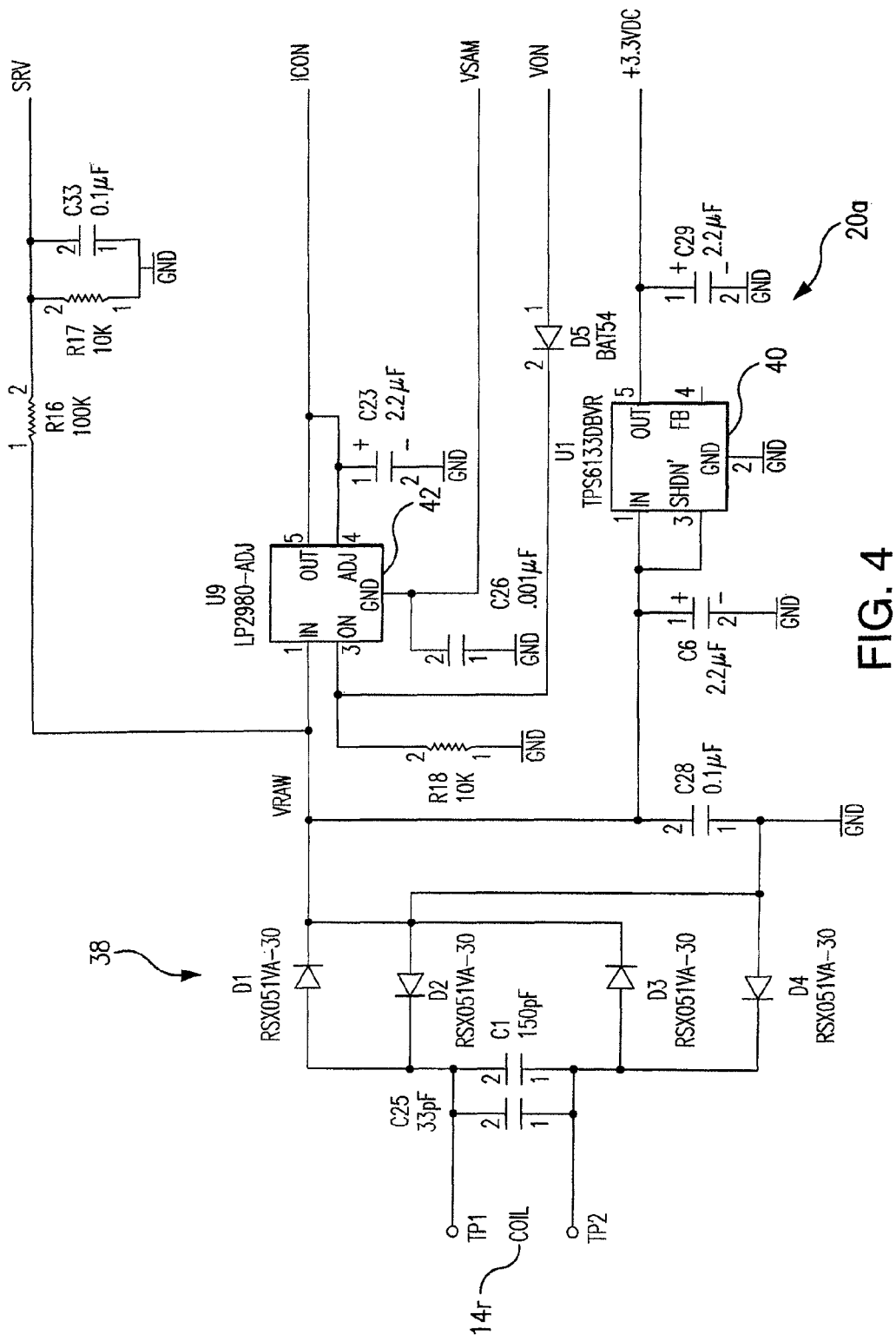
FIG. 4 is a circuit diagram of a portion of the remote circuitry of the inventive brain-monitoring system of FIG. 1, illustrating an embodiment of the power circuitry therein. This embodiment of the remote circuitry is powered exclusively by power transmitted at RF frequencies.
Figure 4A:
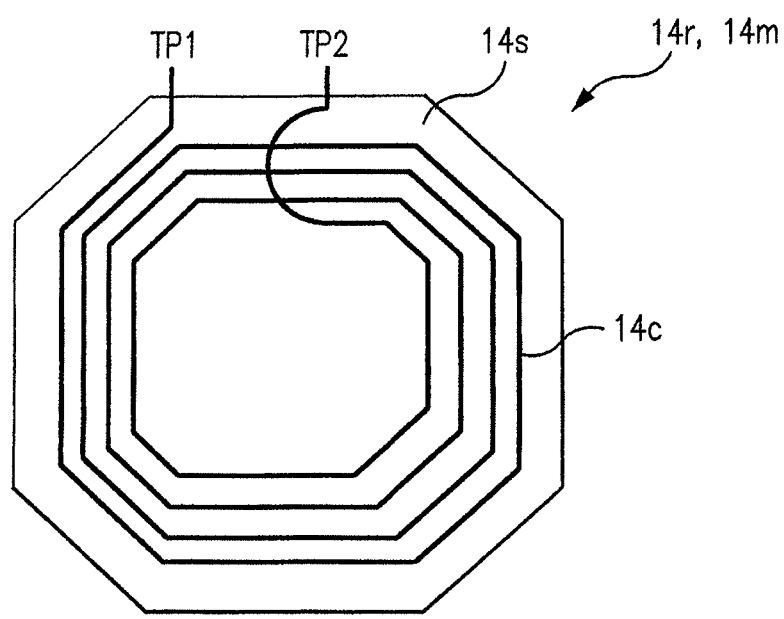
FIG. 4A is a schematic drawing of an RF inductive receive coil within the remote circuitry of the inventive brain-monitoring system of FIG. 1.

FIG. 4 is a circuit diagram illustrating an embodiment of power circuitry 20a within remote circuitry 20. RF inductive receive coil 14r receives power from main circuitry 22 through RF inductive transmit coil 14m, and this power is rectified and conditioned in portion 20a of remote circuitry 20. Four Schottky diodes 38 (also labeled as D1 through D4) are configured as a full-wave rectifier to condition the power. Diodes 38 may be Schottky barrier diodes such as diode RSX051VA-30 available from Rohm Co., Ltd. of Kyoto, Japan. The configuration of all of the components integrated into the remaining circuitry of FIG. 4 is standard and well-known to those skilled in the art of circuit design to provide clean and regulated DC power. Integrated circuit 40 is a low-dropout, low-power linear voltage regulator. Such a chip may be model TPS76133 DBVR available from Texas Instruments Inc. of Dallas, Tex. Integrated circuit 42 is an ultra-low-dropout adjustable voltage regulator. Such a chip may be model LP2980-ADJ available from National Semiconductor of Santa Clara, Calif.

FIG. 4A is a schematic drawing of an RF inductive receive coil within the remote circuitry of inventive brain-monitoring system 10 of FIG. 1. As shown, RF inductive receive coil 14r is a flexible printed circuit coil consisting of metallic conductors 14c deposited onto substrate material 14s such as Mylar film. Coil 14r is connected to power circuitry 20a at points TP1 and TP2 as shown in FIG. 4. Coil 14r is not limited to the configuration as shown in FIG. 4A. For example, coil 14r could be coiled magnet wire in a number of other coil forms. FIG. 4A is also an illustration of inductive transmit coil 14m since one embodiment of coil 14m may be essentially identical to coil 14r.

Figure 5:
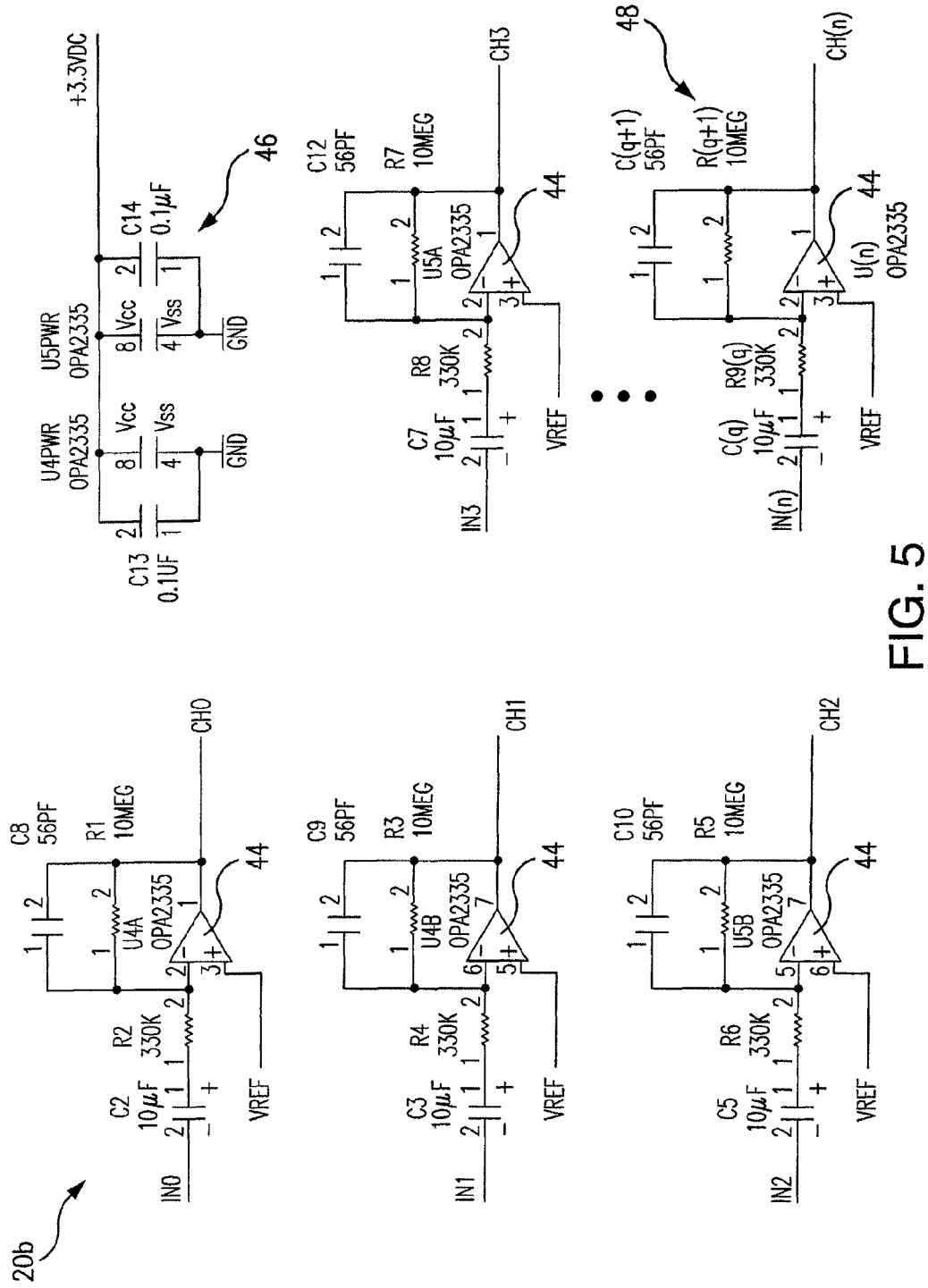
FIG. 5 is a circuit diagram of a portion of the remote circuitry of the inventive brain-monitoring system of FIG. 1, illustrating an embodiment of the instrument amplifiers therein.

FIG. 5 is a circuit diagram illustrating an embodiment of instrument amplifiers 20b within remote circuitry 20. Each electrode 12 requires an amplifier to condition the EEG signal captured thereby. As illustrated in FIG. 5, such amplifiers may be configured using CMOS operational amplifiers in a standard instrument amplifier configuration within accompanying resistors and capacitors as shown in FIG. 5. Such configurations are well-known to those skilled in the art of circuit design. Operational amplifiers 44 (several are shown) may each be one of the two amplifiers in a model OPA2335 integrated circuit CMOS dual operational amplifier chip available from Texas Instruments Inc. of Dallas, Tex. Circuit portion 46 illustrates the power connections to such multiple operational amplifiers 44.

In FIG. 5, the portion of circuitry labeled with reference number 48 illustrates the scaling of circuit portion 20b which allows for the scaling of remote circuitry according to the number (n) of electrodes 12.

Figure 6:
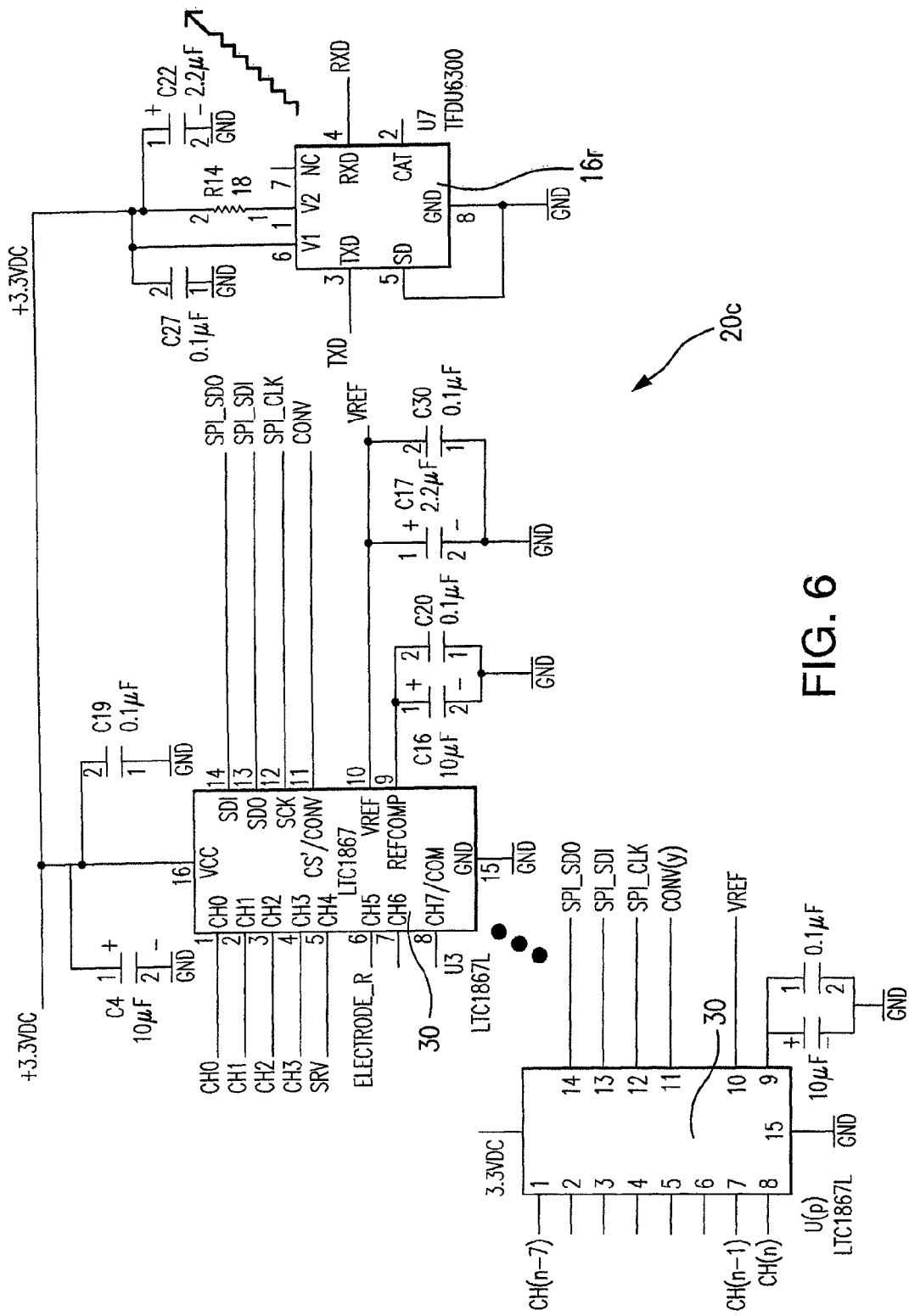
FIG. 6 is a circuit diagram of a portion of the remote circuitry of the inventive brain-monitoring system of FIG. 1, illustrating an embodiment of the A/D converter and IR transceiver therein.

FIG. 6 is a circuit diagram illustrating an embodiment of A/D converter 30 and IR transceiver 16r within remote circuitry 20. A/D converter 30 is connected to the outputs of instrument amplifiers 20b and is configured to be able to select which of the various amplifier (and therefore electrode) outputs to convert to a digital signal. Integrated circuit A/D converter 30 may be a model LTC1867L 16-bit, 8-channel A/D converter chip available from Linear Technology Corporation of Milpitas, Calif. FIG. 6 also illustrates IR transceiver 16r within remote circuitry 20. IR transceiver 16r may be a model TFDU6300 fast IR transceiver chip available from Vishay Intertechnology, Inc. of Malvern, Pa. This transceiver model has a maximum data rate of 4 Mbits per second. If the number of channels (n) increases past the point where this bandwidth is not sufficient, faster transceiver chips are available.

One very significant advantage of this inventive wireless brain-monitoring system is the separation of power and data transmission modes of communicating between remote circuitry 20 and main circuitry 22. This separation assures that the power transmission RF signal can remain at 13.56 MHz rather than being increased to accommodate data transmission in an RF band while the data bandwidth rises as the number (n) of channels grows to be very large as physicians increase the diagnostic demands on such systems.

Micro-controller 20e (see FIG. 8) is programmed in firmware to provide clock and control signals to A/D converter 30 that enable it to select and convert the analog signal from each channel (electrode and instrument amplifier) to a 16-bit digital signal in serial form. Each such 16-bit word is sent to micro-controller 20e and then forwarded to IR transceiver 16r for transmission to main circuitry 22. Programming of such control actions is well-known to those skilled in the art of circuit design and digital system design. IR transceiver 16r and micro-controller 20e, in a similar fashion, are configured to receive IR signals from main circuitry 22 for the control of the various functions carried out by remote circuitry 20.

As with instrument amplifiers 20b in FIG. 5, FIG. 6 includes circuitry to indicate that A/D conversion is scalable to accommodate an increased number of electrodes (and therefore channels) to be converted to digital signals and transmitted. Such scaling requires the addition of more A/D input channels, and FIG. 6 illustrates one approach to such scaling with the addition of another A/D converter 30 integrated circuit, as shown and labeled indicating the accommodation of n channels.

Figure 7A:
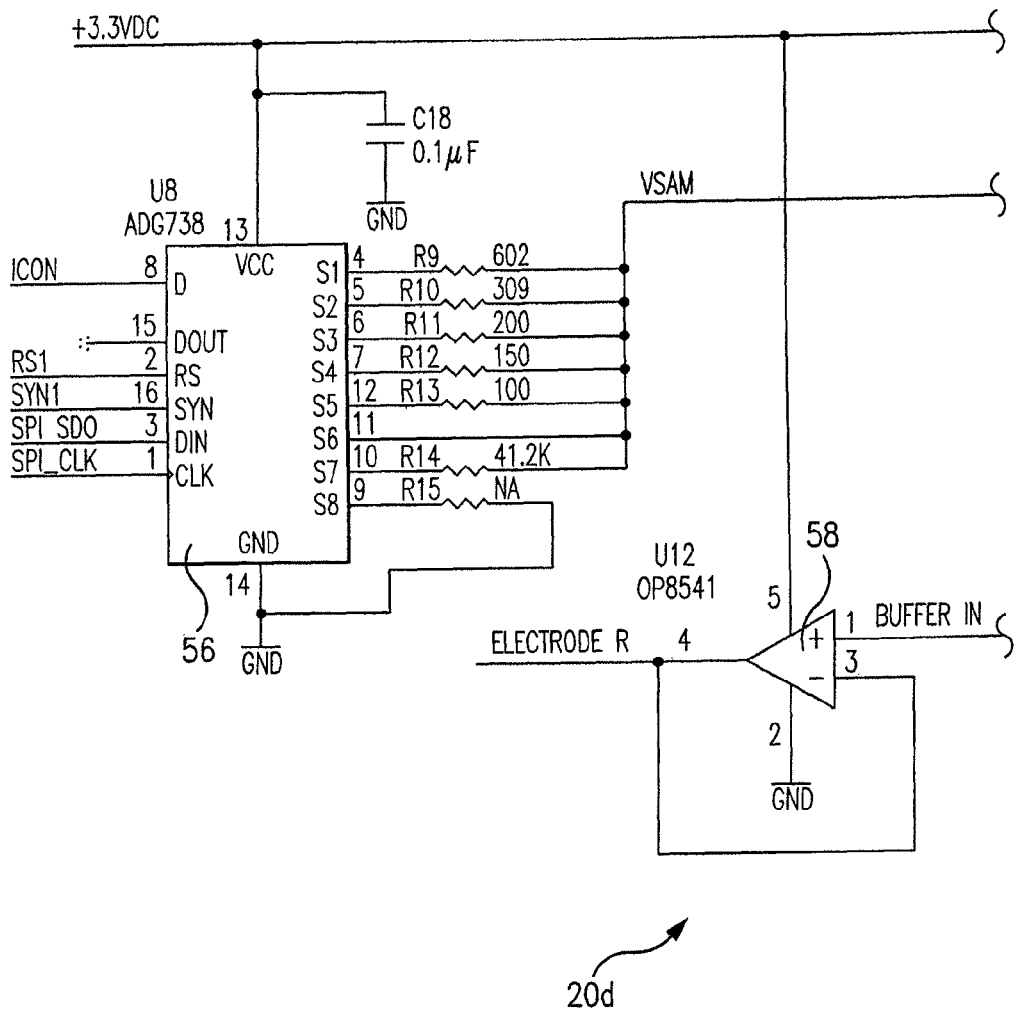
FIG. 7 is a circuit diagram of a portion of the remote circuitry of the inventive brain-monitoring system of FIG. 1, illustrating an embodiment of the analog switch network circuitry therein and including circuitry for tissue stimulation and electrode impedance measurement.
Figure 7B:
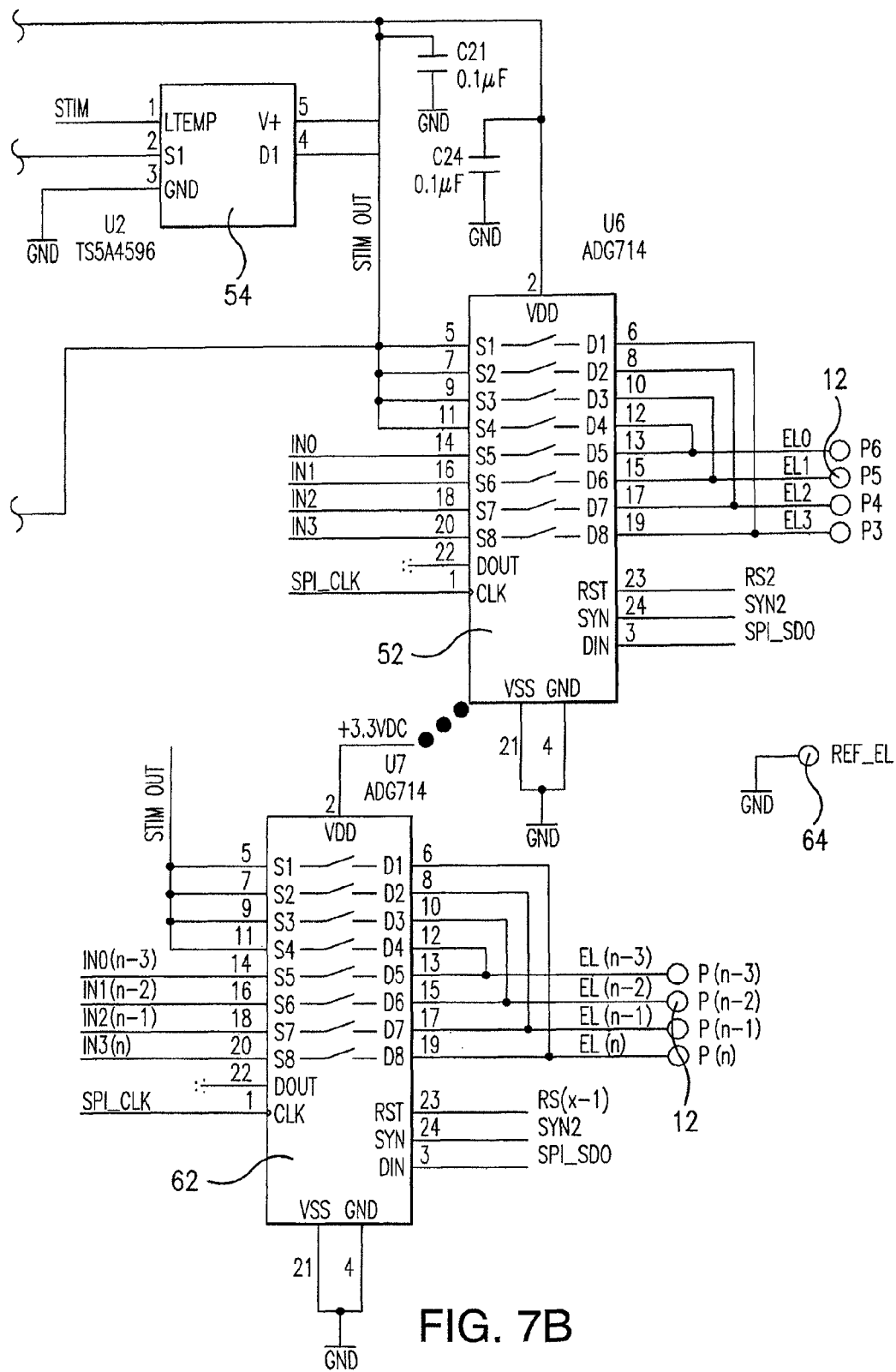

FIG. 7 is a circuit diagram illustrating an embodiment of analog switch network circuitry 20d including circuitry for tissue stimulation and electrode impedance measurement. This portion 20d of remote circuitry 20 includes multiple analog switches configured to enable each electrode 12 to be selected, under the control of programmed micro-controller 20e, to deliver a selected amount of electrical current to the selected electrode 12. Analog switch integrated circuit 52 is configured to select an electrode 12 for delivery of stimulation current. Analog switch 56 is configured to select the amount of stimulation current to be delivered to a selected electrode 12. In this embodiment, current values of 2, 4, 6, 8, and 10 mA are the preselected values of stimulation current, but such values should not be understood to limit the values of current to be supplied. These current values are set by selecting from among pins S1 through S5 of switch 56. Stimulation current flows through switch 54 to control the width of current pulses delivered under control of programmed micro-controller 20e. Typical current delivery is stream of 0.2 msec pulses delivered at a 50 Hz rate for 5 seconds, but such values are not to be understood as limiting in any way with respect to the time history, form, type, and levels of delivered stimulation current to be generated within inventive system 10.

When an electrical impedance measurement is being made, analog switch integrated circuit 56 delivers a low-level electrical current to a selected electrode 12 for an impedance measurement. In this embodiment, the measurement is of a pair of electrodes, the selected electrode and a reference electrode 64 to complete the circuit on which the impedance measurement is taken. In this embodiment, by measuring the electrical impedance of multiple pairs of selected electrodes 12 with reference electrode 64, it will be most often possible to assess the condition of each electrode 12 over time while it is implanted in the brain.

For impedance measurements in this embodiment of remote circuitry 20, a fixed electrical current of about 50 .mu.A is supplied at pin S7 of analog switch 56 for measurements of from 0 to about 40K ohms. A/D converter 30 is used to measure the resulting voltage (and therefore impedance) during a short pulse of the delivered low-level current. The voltage is measured on the line labeled ELECTRODE_R on which the voltage signal if buffered by a unity-gain operation amplifier 58.

Analog switch 52 may be a model ADG714 CMOS, low-voltage serially-controlled octal switch available from Analog Devices of Norwood, Mass. Analog switch 56 may be model ADG738 CMOS, low-voltage, 3-wire serially-controlled matrix switch available from Analog Devices of Norwood, Mass. Analog switch 54 may be model TS5A4596 SPST, single-channel analog switch available from Texas Instruments, Inc. of Dallas, Tex. Operational amplifier 58 may be a model AD8541 general-purpose CMOS rail-to-rail amplifier available from Analog Devices of Norwood, Mass.

As shown in several previous figures, FIG. 7 also includes circuitry to indicate the scalability of the electrode selection, stimulation and impedance measurement functions as the number (n) of electrodes 12 is increased. Analog switch integrated circuit 62 handles the representative increase in the channels to be selected.

Figure 8:
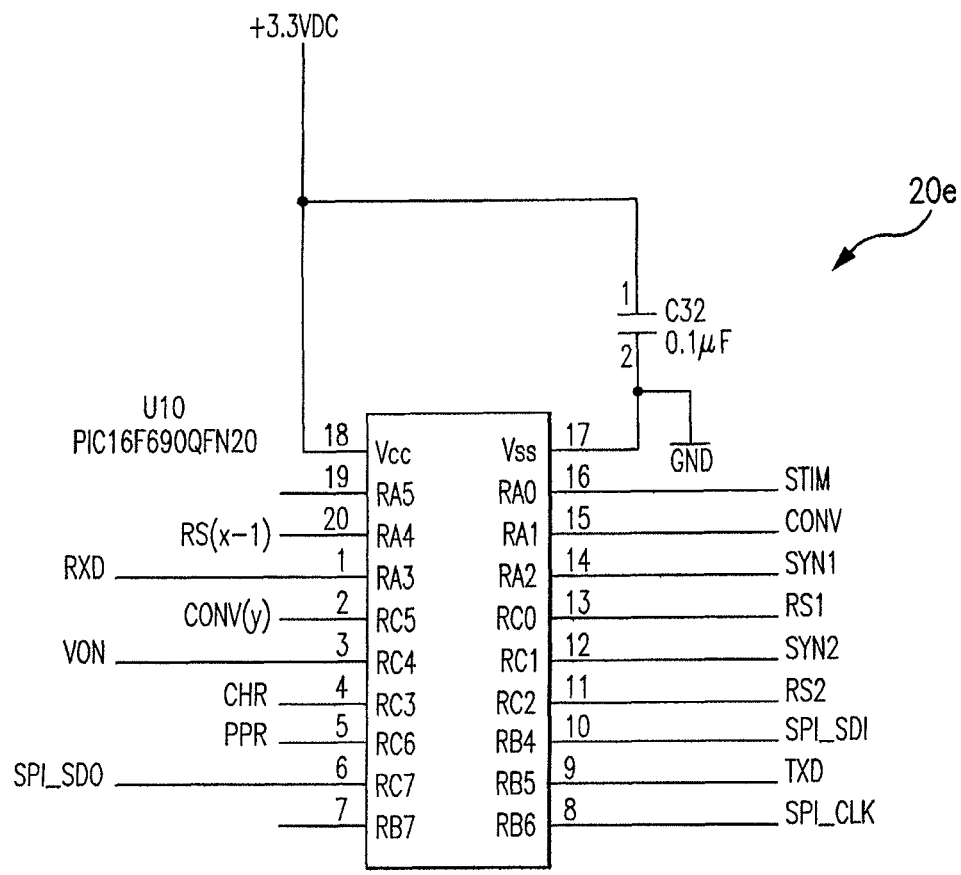
FIG. 8 is a circuit diagram of a portion of the remote circuitry of the inventive brain-monitoring system of FIG. 1, illustrating an embodiment of the micro-controller therein.

FIG. 8 is a circuit diagram illustrating an embodiment of micro-controller 20e within remote circuitry 20. Micro-controller 20e contains programmed instructions stored in firmware to carry out the functions described above. Detailed instructions are not described herein since such instructions are well-known to those skilled in the art of circuit design and digital design. As shown in FIG. 8, micro-controller 20e may be a model PIC16F690QFN20-pin flash-based 8-bit CMOS micro-controller available from Microchip Technology Inc. of Chandler, Ariz. Note that micro-controller 20e is shown with signals to control an expanded number (n) of electrodes 12. However, as n increases, a micro-controller having a sufficiently large number of I/O lines will be required to accommodate such an increase. As shown in FIG. 8, I/O lines RS(x−1), and CONV(y) accommodate additional switches and A/D converters as required.

FIG. 9 is a circuit diagram illustrating an embodiment of the RF power circuitry 22a within main circuitry 22. This circuitry provides 13.56 MHz RF power to be transmitted via RF inductive transmit coil 14m to remote circuitry 20. An oscillator chip 68 generates the 13.56 MHz signal, and a non-inverting buffer amplifier 66 provides the drive current for a class-D amplifier 72. A linear regulator 70 provides the 5 VDC power required by oscillator chip 68 and buffer amplifier 66.

Buffer amplifier 66 may be a model 74HC541 non-inverting buffer integrated circuit available from Texas Instruments Inc. of Dallas, Tex. Oscillator chip 68 may be a model ECS-P53-13.56-A programmable SMD clock oscillator available from ECS Inc. International of Olathe, Kans. Linear regulator 70 may be a model MAX1598 low-dropout linear regulator available from Maxim Integrated Products, Inc. of Sunnyvale, Calif. Amplifier 72 may be a model ZVN4310G DMOS FET available from Zetex Semiconductors plc of Chadderton, Oldham, United Kingdom. Inductor L, may be a 3-turn air coil of 22-gauge magnet wire with an inside diameter of 0.187 inches.

Figure 9A:
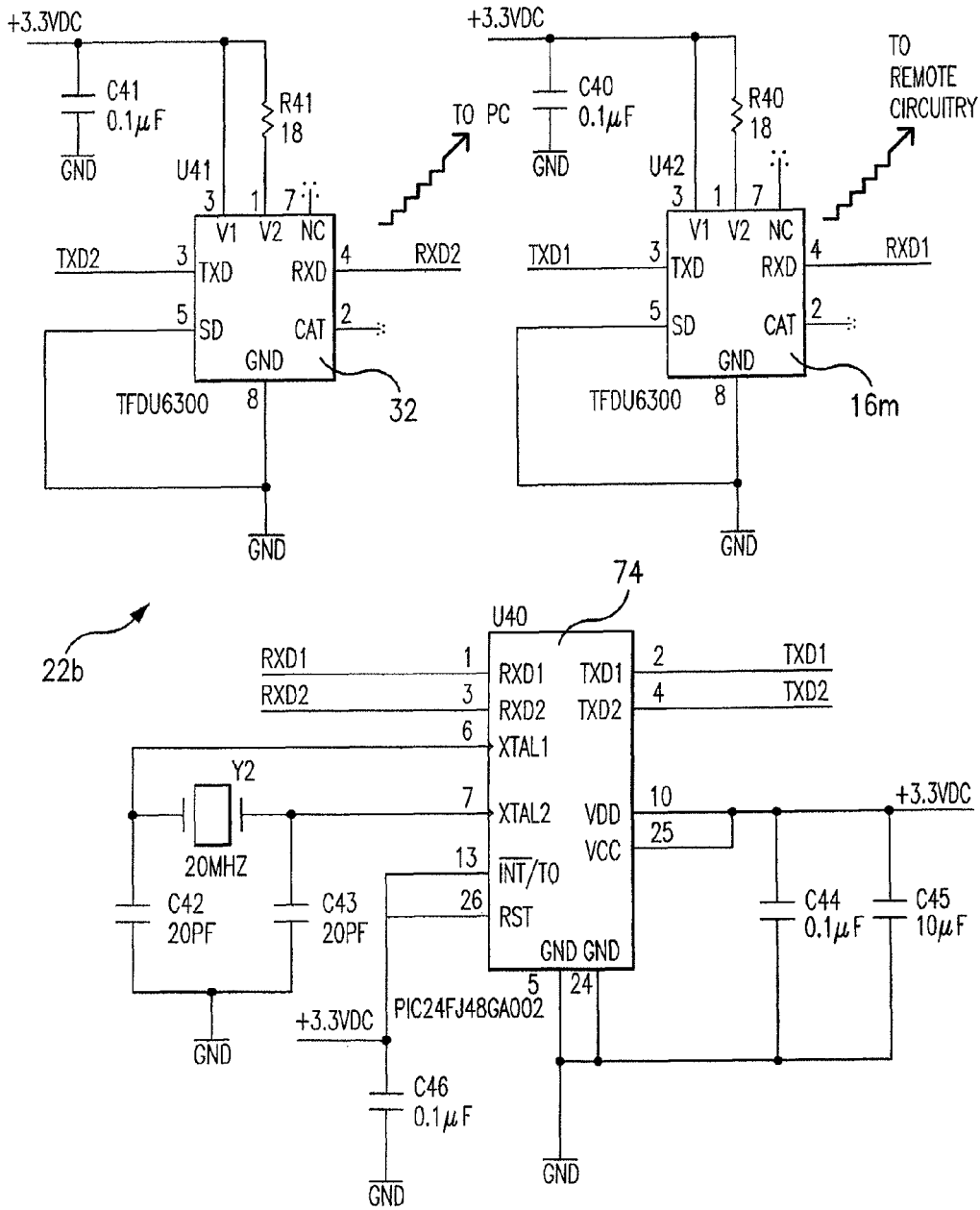
FIG. 9A is a circuit diagram of a portion of the main circuitry of the inventive brain-monitoring system of FIG. 1, illustrating an embodiment of the infrared data link to the remote circuitry.

FIG. 9A is a circuit diagram of the data transmission portion 22b of main circuitry 22 of the inventive brain-monitoring system of FIG. 1, illustrating an embodiment of the infrared data link to remote circuitry 20. FIG. 9A also illustrates an infrared data link to the computer (PC) which communicates with main circuitry 22 over another such data link. Two IR transceiver integrated circuits 16m and 32 are shown. IR transceiver 16m communicates with remote circuitry 20, and IR transceiver 32 communicates with the computer (PC) as is illustrated in FIGS. 1 and 3. Data transmission circuitry 22b also includes a micro-controller 74, including stored firmware instructions, which controls the functions of IR transceivers 16m and 32. Such firmware instructions are well-known to those skilled in the art of digital design and are not discussed in further detail herein. The interconnections necessary to carry out such functions are shown in FIG. 9A.

IR transceivers 16m and 32 may be the same integrated circuits as IR transceiver 16r. Micro-controller 74 may be a model PIC2444FJ48GA002 16-bit micro-controller available from Microchip Technology Inc. of Chandler, Ariz.

Figure 10A:
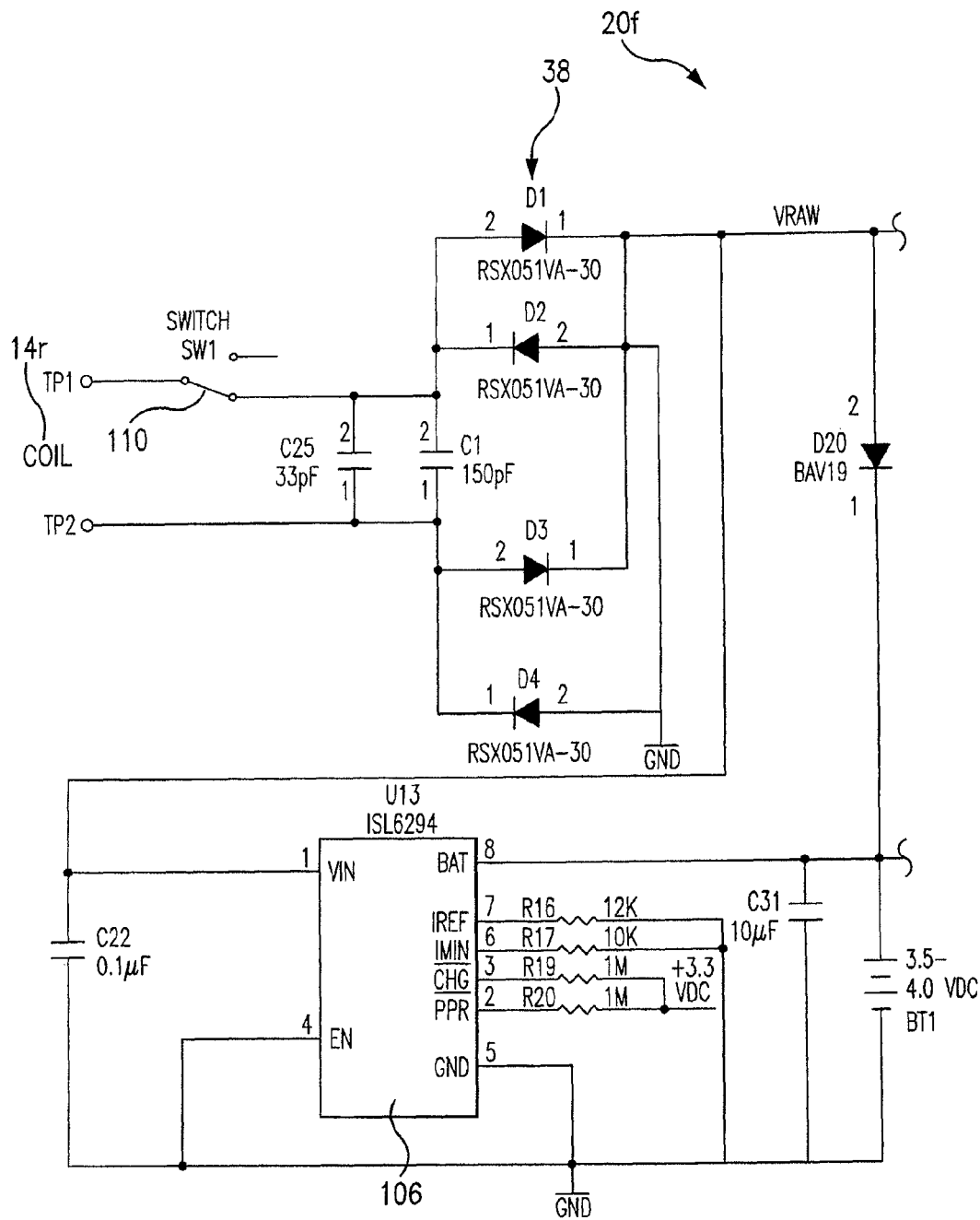
FIG. 10 is a circuit diagram of a portion of the remote circuitry of the inventive brain-monitoring system of FIG. 1, illustrating an alternative embodiment of the power circuitry therein including a solid-state lithium rechargeable battery and power capacitor.

FIG. 10 is a circuit diagram of a portion 20f of the remote circuitry 20 of the inventive brain-monitoring system of FIG. 1, illustrating an alternative embodiment of the power circuitry including a solid-state lithium rechargeable battery BT1. Portion 20f of remote circuitry 20, in addition to solid-state lithium rechargeable battery BT1, includes a power capacitor C31 and a single-cell Li-ion battery charger integrated circuit 106. Four Schottky diodes 38 (also labeled as D1-D4) are configured as a full-wave rectifier to condition the power as in portion 20a in FIG. 4. The configuration of all of these components integrated into the remaining circuitry of FIG. 10 is standard and well-known to those skilled in the art of circuit design. Battery charger integrated circuit 106 may be a model ISL6294 integrated circuit available from Intersil Corporation of Milpitas, Calif.

Battery BT1 may be a flexible, thin-film battery such as is available from ITN Energy Systems of Littleton, Colo. Such solid-state lithium rechargeable batteries utilize stable, safe, reversible chemistry and have a high power density. Also, batteries of this type can be cycled more than 10,000 times and have a long shelf life. As a solid-state (dry) component, such a battery is ideal for use in a medical implant. The physical configuration of such a battery is also ideal for miniaturization within an implant device.

Power capacitor C31 is positioned to store charge across battery BT1 such that if remote circuitry 20 should require a higher current for short periods of time than can be provided by the RF transmission source or battery BT1, capacitor C31 in a charged state can meet such current demand.

Steering diodes 112 and 114 (also labeled D20 and D21, respectively) allow power to flow from the higher voltage of the two sources, battery BT1 and power capacitor C31 or voltage VRAW provided by RF power transmission. VRAW also provides power to the charging circuit.

Remote circuitry 20 may be configured with either power capacitor C31 or battery BT1 (and related charging circuitry) or both as illustrated in FIG. 10. Depending on these alternatives, remote circuitry 20 is configured in standard ways as are well known by those skilled in the state-of-the-art of circuit design.

FIG. 10 also illustrates a switch 110 which serves as a circuit-loop-interrupting element. Switch 110 may be a miniature mechanically-actuated switch which is positioned to be actuated through the skin. Switch 110 is placed in its OPEN position when it is necessary to expose the patient being monitored into an MRI environment. Actuation of switch 110 back into its CLOSED state is carried out in a similar fashion. As illustrated in FIG. 10, switch 110 interrupts a circuit loop formed by coil 14r (not shown in FIG. 10) connected between points TP1 and TP2. Opening such a circuit loop reduces the effect of induced electrical currents in remote circuitry 20.

FIG. 11 is a schematic illustration of a possible physical configuration showing the inclusion of battery 122 (identified as BT1 in FIG. 10) in the packaging of remote circuitry 20 within the alternative embodiment of FIG. 10. FIG. 11 is highly schematic in that the integrated circuits IC1-IC4 shown on the circuit board 120 are only representative and do not correspond to particular integrated circuits within remote circuitry 20 shown in FIG. 10. Battery 222 is shown as a thin-film component mounted on one side of a circuit board 220 on which remote circuitry 20 has been placed.

A video camera may be aimed at the patient during monitoring and mapping using wireless system 10. A video camera (not shown) typically generates a stream of time stamps to identify precisely the time at which a video frame is captured. Wireless system 10 can be synchronized with the video stream from the camera by synchronizing the digital stream of data being transmitted from remote circuitry 20. One possibility is to create a synchronizing time mark in the data stream from remote circuitry 20 by triggering a single stimulation event at a known video time stamp. Subsequent analysis of the data stream from remote circuitry 20 can be done with precise knowledge of the related video imagery.

It is desirable to package remote circuitry 20 in as small a package as possible. Accordingly, remote circuitry 20 may be produced using ASIC technology (application-specific integrated circuits), integrated circuits which achieve a high degree of integration and size reduction. Remote circuitry 20 as illustrated in the embodiments of FIGS. 4, 5 through 8, and 10 is shown as being constructed using discrete components, but such illustration is only for purposes of explanation and should not be taken as limiting in any way as to how remote circuitry 20 should be physically configured. It should be noted that either with discrete integrated circuits or with an ASIC, very low power devices may be used to keep the power consumption as low as possible in remote circuitry 20.

The wireless monitoring system 10 disclosed above (that is, a device employing 4 EEG channels and 1 reference channel) includes a separate amplifier and A/D converter within the remote circuitry for each EEG channel. In accordance with an alternate embodiment, and with reference to FIGS. 12 to 14, an alternate embodiment of the wireless monitoring system 110 including remote circuitry for 64 EEG channels and 1 reference channel is disclosed. With the exception of the distinctions discussed below, in particular, in relation to the incorporation of a multiplexer 180 into the wireless monitoring system 110, the structure of the remote circuitry 120 and the main circuitry 22 is similar to the embodiment described above. As such, and as with the prior embodiment, the remote circuitry 120 includes an RF inductive receive coil 114r and an infrared transceiver 116r for transmitting and receiving data with an infrared signal across the skin 18 of the patient being monitored. The IR transceiver 116r is aligned with a hole in the patient's skull in order to transmit and receive IR signals through skin 18.

The present wireless monitoring system 110 also includes main circuitry 22. The main circuitry 22 includes an RF inductive transmit coil 14*m* to transmit power to remote circuitry 120 and an IR transceiver 16*m* to receive data from and send data to remote circuitry 120. Both inductive transmit coil 14*m* and transceiver 16*m* are located at the end of cabling 26 for the main circuitry 22 such that these elements can be conveniently positioned with respect to the head of the patient being monitored. RF inductive receive coil 114*r* within remote circuitry 120 receives power from an RF inductive transmit coil 14*m* which is part of main circuitry 22.

As mentioned above, and in contrast to the previously described embodiment, the wireless monitoring system 110 includes a multiplexer 180 within the signal path of the remote circuitry 120. This change allows a single amplifier 120*b* and a single A/D converter 130 to be employed for multiple channels; allowing for scaling of the number of channels being recorded without an increase in space requirements, power consumption, and heat generation.

In accordance with a preferred embodiment, the wireless monitoring system 110 samples each electrode 112 at a rate that is at least twice the highest frequency of the electrode signal. For example, if the desired bandwidth is 500 Hz then the sampling frequency is at least 1 KHz (Nyquist rate). Anti aliasing filtering at the input of each channel, that is, electrode 112 connected, to the multiplexer 180 is achieved by the provision of an array of series L (as ferrite beads) and shunt capacitors 182 at the input of each channel on the multiplexer 180. In addition to limiting the frequency content of the input signal to be measured, the provision of an array of series L and shunt capacitors 182 at the input of each channel to the multiplexer 180 also filters out unwanted noise and the RF field powering the circuit.

The sampling duration is determined by the number of channels and the highest frequency of the signal. For example, and in accordance with an embodiment with 64 channels, if there are 64 channels and the highest frequency component of the signal is 500 Hz then the sampling rate would be 64 KHz and each channel would be sampled once every 1 msec for an interval of 15.6 μsec. It is important to measure each channel after the circuitry has had time to settle so there are no switching artifacts introduced into the measured signal.

The multiplexer 180 employed in accordance with a preferred embodiment of the present invention is effectively DC coupled. The circuit is AC coupled but the rapid switching of the multiplexer 180 and electrodes 112 makes it able to measure instantaneous DC voltages. The multiplexer 180 includes a low pass filter 184 at each channel input 186 and should be able to operate with an input potential of at least 100 millivolts above or below ground to accommodate the potentials measured within the human body. The DC power to the coupler is filtered with capacitors to reduce the noise from the other circuitry and the RF field powering the remote circuitry 120. A resistor to ground is also provided at each channel input 186 to bleed off charge between measurement intervals.

The largest number of channels commercially available on a multiplexer is currently 32 channels. It is, therefore, appreciated the number of input channels can be increased by utilizing parallel multiplexers 180, 180*b*. Where parallel multiplexers 180, 180*b* are employed in accordance with the present invention, the address lines can be paralleled and the Enable pin 188, 188*b* is used to select specific multiplexers. The rapid switching of the channel inputs 186 of the multiplexer 180 produces a high frequency signal at the output 190 of the multiplexer 180. That high frequency signal at the output 190 of the multiplexer 180 is modulated with the voltages of the electrodes 112 of the selected channels.

For example, and in accordance with a preferred embodiment employing 64 channels sampled at a 1 KHz per channel rate as discussed above, the output high frequency signal is a 15.6 μsec (64 KHz) pulse that has 64 consecutive pulses modulated with the amplitude of each of the 64 channels, then it repeats over. The order or number of channels is set by the micro-controller 120*e*.

It is appreciated the multiplexer chosen for use in accordance with the present invention should have low channel resistance so the waveform can be acquired quickly with little attenuation and should also have low capacitance at the output so the circuit can respond to the rapidly changing channels.

As mentioned above, the present wireless monitoring system 110 includes an amplifier 120*b*. In accordance with a preferred embodiment, the amplifier 120*b* is a high speed op amp that amplifies pulses modulated by the selected channels. The gain of the amplifier 120*b* is about 25 dB. The pulses for a 64 KHz system sampled at 1 KHz are 15.6 μsec in width. The amplifier 120*b* should have very low noise and respond with no overshoot or ringing. Ringing in the amplifier 120*b* can cause crosstalk into adjacent channels. A roll off capacitor is used in the feedback circuit to reduce the amplifier bandwidth for increased signal to noise ratio.

Only one amplifier 120*b* is needed for all the channels of the present wireless monitoring system 110. The ability to amplify 64 channels of information with a single amplifier 120*b* achieves similar gain, offset and noise characteristics for all channels. Since the signals are high speed pulse signals, they are removed from low frequency noise such as Shot Noise and a small coupling capacitor can be used to couple the signal into the op amp.

The amplifier 120*b* is designed with additional circuitry capable of measuring DC voltages at the electrodes 112. The DC level is converted to pulse amplitude by the switching of the multiplexer 180.

The amplified signals are digitally converted by an A/D converter 130. The A/D converter 130 is a high speed 16 bit converter. The reference voltage for the A/D converter 130 is generated through a low noise reference voltage diode which serves to isolate the converted signal from power supply noise. The A/D converter 130 also has capacitors on the power supply to reduce noise. The A/D converter 130 is controlled by the micro-controller 120*e*. As with the prior embodiment, the micro-controller 120*e* is an 8-bit microcontroller.

The micro-controller 120*e* controls the A/D converter 130, the multiplexer(s) 180, 180*b*, the IR transceiver 116*r* and measures the power supply voltage. The micro-controller 120*e* receives commands and transmits data via the infrared transceiver 116*r*. The micro-controller 120*e* is programmable on the circuit board. The micro-controller 120*e* is also capable of receiving commands that instruct which channels to measure and to set the sampling rate. If a particular set of channels have signals of interest, it is possible it measure them with higher time resolution to increase waveform fidelity. It is also possible to ignore other channels if the signals are not useful or if the electrodes are damaged. In high noise environments, the micro-controller can measure and transmit channels multiple times to insure good data is received by the device outside of the body. Some multiplexer channels can also be used for sensors for other modalities such as ECG electrodes, temperature sensors, blood pressure sensors, biosensors to measure pH, potassium, glutamate, GABA (gamma-aminobutyric acid) and the like and not have to be sampled at the same rate as EEG signals. The micro-controller can select the appropriate sampling for these channels. By sensing the input voltage to voltage regulator the micro-controller can adjust the duty cycle, speed or data rate of the circuitry in proportion to the available power from the RF field. The micro-controller can also regulate the charging of the rechargeable battery taking into account the power used by the circuitry. In other words it can divide the power from the voltage regulator between the battery and circuitry depending on the available power and power requirements of the circuitry. This can greatly extend battery life and reduce the RF field needed to power the implant. In accordance with a preferred embodiment, the current used to charge the battery would be scaled depending upon available power. The charge rate of the battery charger would be changed according to available power. This can be accomplished by the micro-controller setting an A/D voltage on the battery charger IC or by the micro-controller selecting a suitable charging resistor in the charging circuit.

As with the prior embodiment, data and control communication is conducted over a standard IR data link. Each data frame transmitted by the implanted device, in particular, the remote circuitry 120, contains data for 64 channels, communication start and stop information and communication error detection information. When a frame is received by the main circuitry 22 a time-stamp is inserted into it. This time-stamp allows the intracranial EEG data stream to be synchronized with a video data stream, thus allowing the EEG and video streams to be viewed in a synchronized manner.

The infrared transceiver 116r uses an infrared diode to transmit infrared signals through the body to an external infrared transceiver 16m or the main circuitry 22 and has an infrared photodiode to receive signals from an external transmitter. Since the Vishay infrared transceiver uses 2.2 volts and the supply voltage is 3.3 volts, another infrared diode is placed in the supply voltage for the transmitter part of the IR transceiver. This diode is then modulated along with the Vishay transmit diode. This increases the infrared signal power and increases the viewing angle at no additional cost in power. The infrared transceiver 116r is controlled by the micro-controller 120e and the data rate is adjustable.

Figure 15:
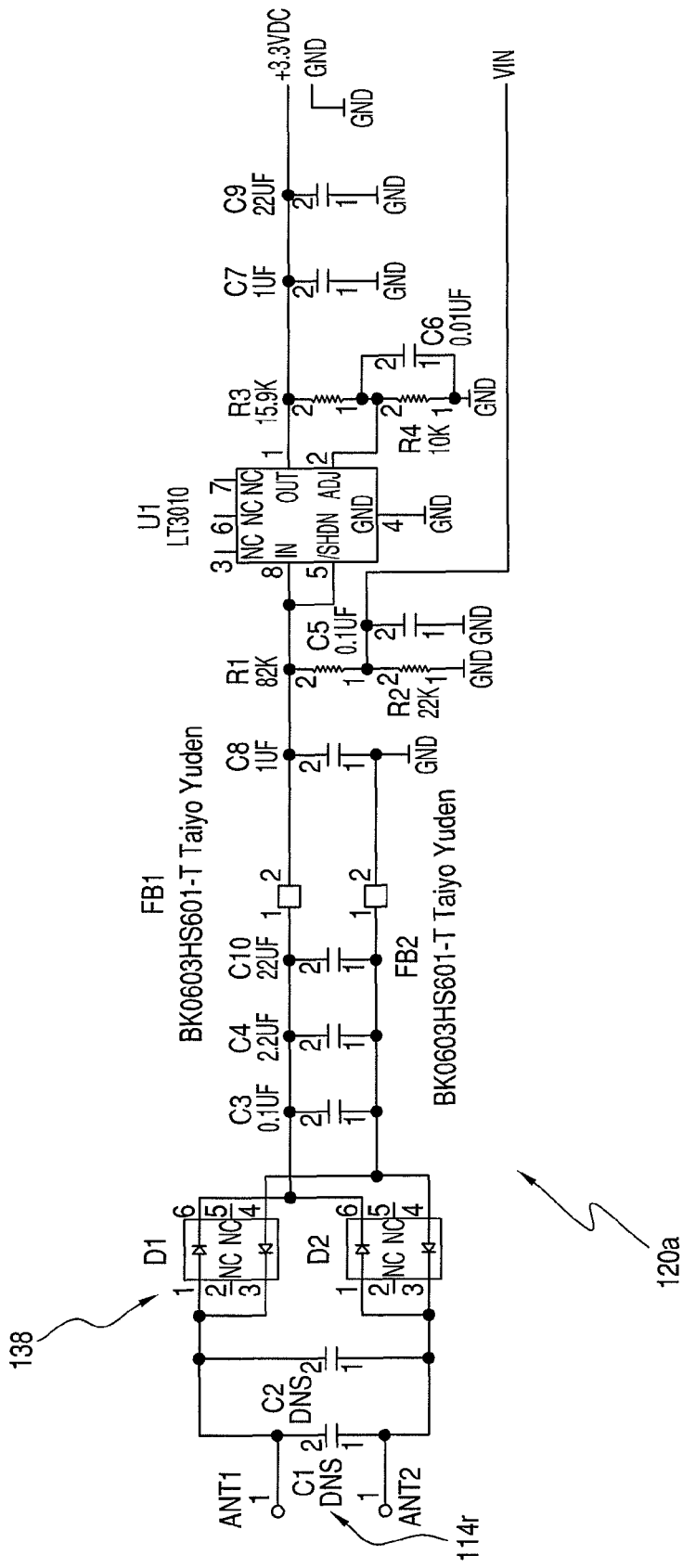
FIG. 15 is a circuit diagram of a portion of the remote circuitry of the inventive brain-monitoring system of FIGS. 12 and 13, illustrating an embodiment of the power circuitry therein. This embodiment of the remote circuitry is powered exclusively by power transmitted at RF frequencies.
Figure 16:
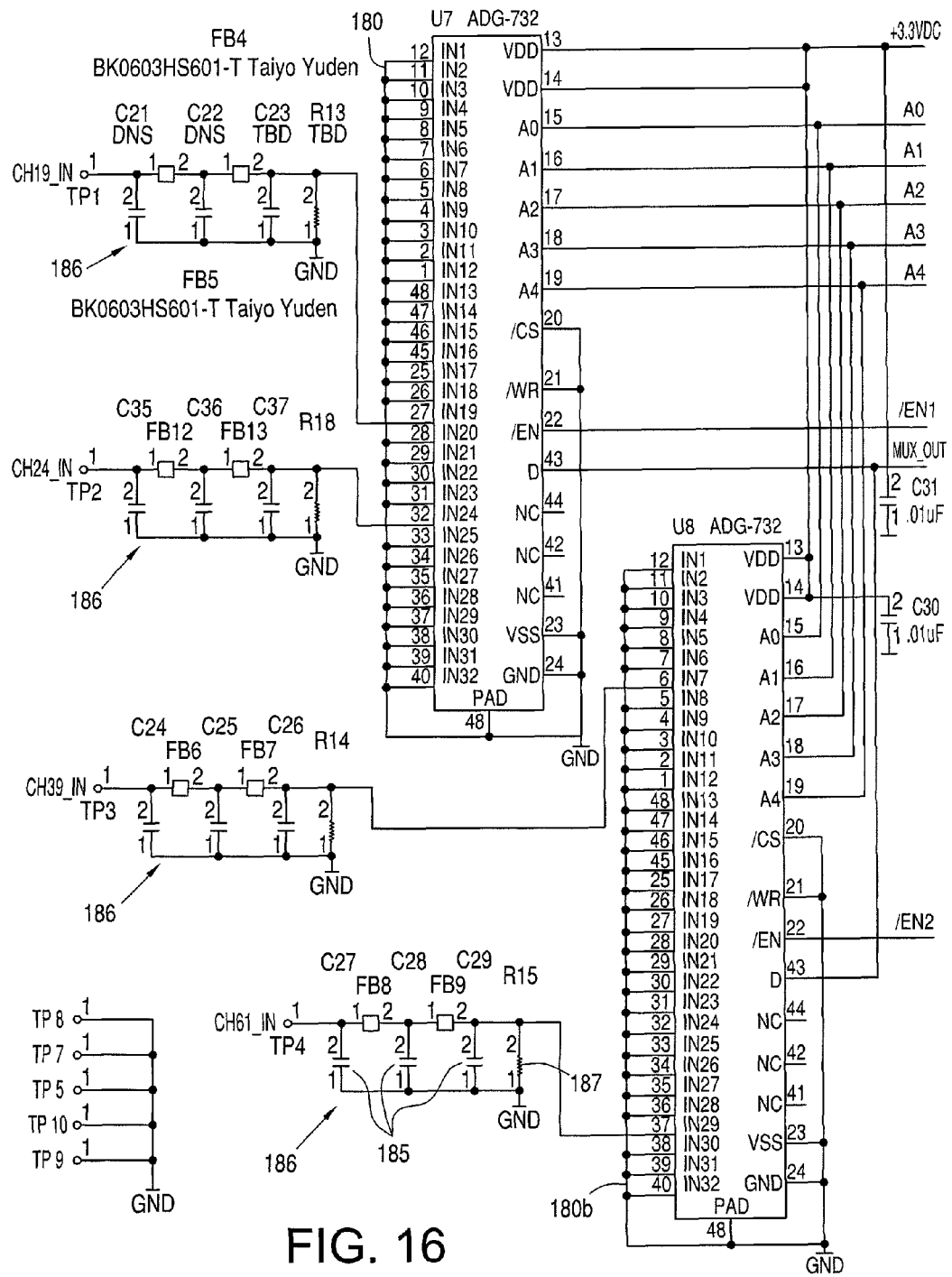
FIG. 16 is a circuit diagram of a portion of the remote circuitry of the inventive brain-monitoring system of FIGS. 12 and 13, illustrating an embodiment of the multiplexer therein.
Figure 17:
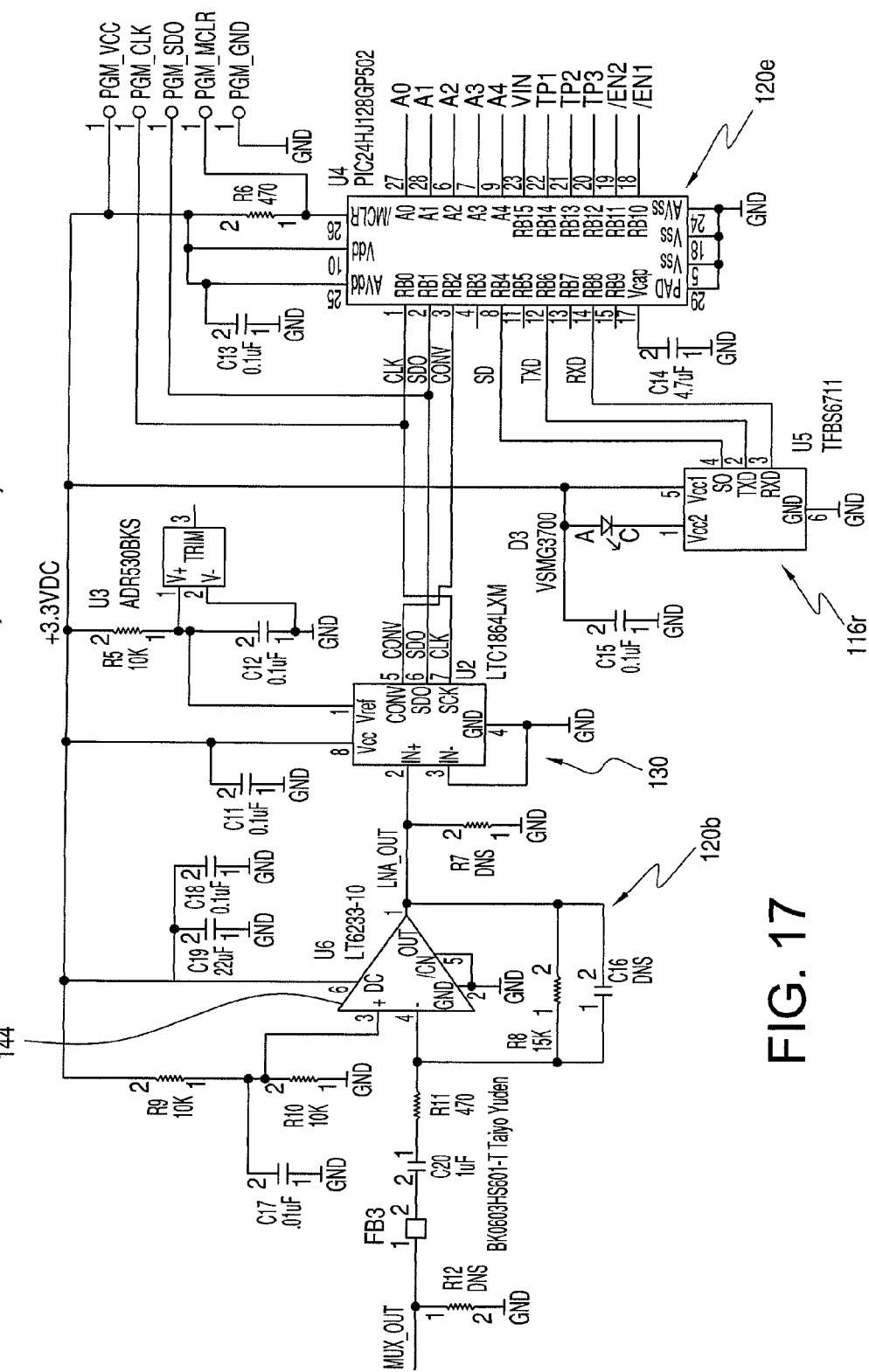
FIG. 17 is a circuit diagram of a portion of the remote circuitry of the inventive brain-monitoring system of FIGS. 12 and 13, illustrating an embodiment of the multiplexer therein.

With reference to FIGS. 15, 16 and 17 circuit diagrams of the embodiment illustrated and described generally in FIGS. 12, 13 and 14 are provided. Each of these figures shows a portion of remote circuitry 120 making up the present embodiment of inventive brain-monitoring system 110. The portions of remote circuitry 120 are interconnected as labeled in the figures, according to standard practice within the field of circuit design, illustrating the various points at which the portions of remote circuitry 120 are joined.

In this embodiment, and as with the previously disclosed embodiment of monitoring system 10, RF power is transmitted from main circuitry 22 to remote circuitry 120 preferably at a frequency of 13.56 MHz. This frequency is particularly well-suited to such an application since, as an FCC-designate ISM band set aside for industrial, scientific and medical devices, the band of 13.553 to 13.567 MHz (centered on 13.560 MHz) is the ISM band which has the lowest loss and least heating of body tissue. (See the Handbook of Biological Effects of Electromagnetic Fields by Polk and Postow, CRC Press, p. 88-91, 1991.) Biological tissue at 13.56 MHz has the lowest conductivity which means that the RF signal will penetrate the tissue to the greatest depth at this frequency.

At a frequency of 13.56 MHz, inductive receive and transmit coils such as 114r and 14m primarily create a magnetic field confined with the locality around the coil. The field diminishes rapidly with distance from the coil, much more rapidly than an electric field under the same circumstances. Thus, the fields which couple the coils are the near fields of the coil. The near field contains the propagating field, the energy storing both the electric and magnetic fields. In the near field, there is much more energy per unit volume available than in the far field; therefore, a higher degree of coupling can be achieved than in the far field alone, thereby increasing the energy transfer efficiency of the circuits.

FIG. 15 is a circuit diagram illustrating an embodiment of voltage regulator (or power) circuitry 120a within remote circuitry 120. RF inductive receive coil 114r receives power from main circuitry 22 through RF inductive transmit coil 14m, and this power is rectified and conditioned in voltage regulator circuitry 120a of remote circuitry 120. As with the embodiment disclosed with reference to FIGS. 1 to 11, Four Schottky diodes 138 (also labeled in pairs as D1 and D2) are configured as a full-wave rectifier to condition the power. The diodes may be Schottky barrier diodes such as diode RSX051VA-30 available from Rohm Co., Ltd. of Kyoto, Japan. The configuration of all of the components integrated into the remaining circuitry of FIG. 15 is standard and well-known to those skilled in the art of circuit design to provide clean and regulated DC power.

FIG. 14 is a schematic drawing of an RF inductive receive coil within the remote circuitry of inventive brain-monitoring system 110 of FIGS. 12 and 13. As shown, RF inductive receive coil 114r is a flexible printed circuit coil consisting of metallic conductors 114c deposited onto substrate material 114s such as Mylar film. Coil 114r is connected to voltage regulator circuitry 120a at points ANT1 and ANT2 as shown in FIG. 15. Coil 114r is not limited to the configuration as shown in FIG. 14. For example, coil could be coiled magnet wire in a number of other coil forms. FIG. 14 is also an illustration of inductive transmit coil 14m since one embodiment of coil 14m may be essentially identical to coil 14r.

FIG. 16 illustrates a preferred embodiment of the dual multiplexer 180, 180b arrangement described above. In accordance with a preferred embodiment, the multiplexers 180, 180b are ADG-732 monolithic CMOS 32 channel/dual 16 channel analog multiplexers available from Analog Devices of Norwood, Mass. Representative channel inputs 186 are disclosed. Each channel input 186 includes a low pass filter 184. In addition, the DC power to the coupler is filtered with capacitors 185 to reduce the noise from the other circuitry and the RF field powering the remote circuitry 120. A resistor 187 to ground is also provided at each channel input 186 to bleed off charge between measurement intervals. The configuration of the components integrated into the remaining circuitry of FIG. 16 is standard and well-known to those skilled in the art of circuit design to provide for the multiplexing of the channel signals received from the various electrodes 112.

In particular, the multiplexers 180, 180b take a low frequency signal (that is, the EEG signal from the electrodes 112) and "chop" it at a high rate to make it a 64 KHz signal. The resulting signal appears as a narrow pulse (15 μsec) every 1 msec. This is combined with 63 other channels to give 64 consecutive pulses of 15 μsec each. The amplitude of each pulse is the instantaneous amplitude of the sampled low frequency signal on each of the 64 channels. The high frequency amplifier 120b sees a signal of 64 KHz and amplifies it. The signal is actually a sampled composite (1 KHz sample rate) of the 64 channels of low frequency signal. 1 KHz is the Nyquist sampling rate for a low frequency signal containing components to 500 Hz. As explained herein in greater detail, the output of the amplifier 120b is then A/D converted by the A/D converter 130, and sent to the computer (PC) via infrared where it is synchronously detected and reassembled back in to 64 channels of low frequency signals.

FIG. 17 illustrates the micro-controller 120e, amplifier 120b, infrared transceiver 116r and A/D converter 130 of the remote circuitry 20. As noted the output of the multiplexer 180, 180b is input to the amplifier 120b which is preferably configured using an operational amplifier 144 in a standard instrument amplifier configuration within accompanying resistors and capacitors as shown in FIG. 16. Such configurations are well-known to those skilled in the art of circuit design. Operational amplifier 144 may be a model LT6233-10 integrated circuit operational amplifier chip available from Linear Technologies Corporation of Milpitas, Calif. The output of operational amplifier 144 is communicated with the A/D converter 130 which is ultimately linked to the micro-controller 120e and the infrared transceiver 116r in a conventional manner. Such configurations are well-known to those skilled in the art of circuit design. In accordance with a preferred embodiment, the A/D converter may be an LTC1864 16-bit A/D converter available from Linear Technologies Corporation of Milpitas, Calif., the micro-controller may be a PIC24HJ128GP502 micro-controller available from Microchip Technologies Inc. of Chandler, Ariz., and the infrared transceiver may be a TFBS6711 low profile infrared transceiver available from Vishay Electronic GmbH, Selb, Germany.

With reference to FIGS. 4 and 14, and as briefly discussed above, the antenna, that is, the coil inductive receive coil 114r of the remote circuitry 120, is used to receive a 13.56 MHz magnetic field signal which is rectified and applied to a voltage regulator. The antenna output is a balanced output with both signal legs rectified and filtered. One of the filtered outputs is applied to ground, the other to the voltage regulator. The filtering of the dual legs is to keep the 13.56 MHz signal from entering in to the circuitry. The antenna is a coil that is parallel tuned with capacitors to 13.56 MHz. The coil can take the form of wires, printed traces and have a center slug of permeable material to increase the magnetic field passing through the coil. The slug would reduce the amount of external RF field to achieve a given power level in the implant. The antenna can range in size from about 2.5 sq in down to less than 0.25 sq in. The small antenna would be used in cases such as when the RF transmit antenna is collocated over the implant antenna. The larger antenna would be used in roaming animals. Antennas in close proximity have stronger coupling and less loss.

The power supply is a straight low noise linear low drop out regulator. A linear regulator has much less noise than a switching regulator. For a 3.3 volt output the linear regulator requires a voltage of at least 3.5 volts on the input. The regulator can regulate with input voltages in excess of 20 volts.

As with the prior embodiment, the electrodes 112 are connected by an analog switch network 120d (as explained in detail with reference to FIG. 7). The analog switch network 120d creates connections between individual electrodes and functional circuitry 128 which provides tissue stimulation current and which enables remote circuitry 120 to measure electrode impedance (detailed in FIG. 7) under the control of the microcontroller 130.

The IR transceiver 16m of the main circuitry 22 is an infrared transmitter and receiver. It can be as simple as a standard IrDA dongle that plugs into the USB port of a computer. It operates on standard IrDA formats. It communicates bidirectionally with the IR transceiver 116r in the remote circuitry 120. If necessary the viewing angle of the infrared link can be increased by placing it in an environment that has reflective surfaces in the infrared region.

Referring to FIG. 4a, the external RF transmitter 14m is a 13.56 MHz CW transmitter. The signal is received by the antenna 114r and rectified to power the implant. The transmitter 14m uses a transmit coil to generate the RF field. The coil can be large (1 sq ft) to power the implant in a moving animal or very small (<0.25 sq in) when used in humans and collocated with the implant antenna. Less RF power is needed if the implant and external antenna are close together. The coupling between the antennas is optimized when they are of the same dimensions and shape. The RF transmitter power can range from 250 mW to over 5 watts depending on the coupling distance and orientation between the antennas. The RF transmitter power can be adjusted to adjust the voltage input to the power supply in the implant. The micro-controller measures the supply input voltage and sends this data out through the IR transceiver 116r. This information can be used to adjust the output power of the external RF transmitter 14m.

It is further appreciated powering of the wireless monitoring system of the present invention may be achieved through long-range wireless power. Although the embodiments described above utilize near field solutions, far field sources have been contemplated in accordance with the present invention. Integrated circuits are now available which would allow for the use of far field antenna (placed for example around the walls of a ward room or a patient's bed room or living room), working at 800 or 900 Mhz, and used to power the present wireless monitoring system. It is further appreciated, a solution of this sort could be used to power a device in a MRI magnet as well.

It is also contemplated power to the device may be supplied through ambient fields. For example, it is contemplated parasitic power may be employed, for example, by tuning into high 60 Hz or a cell phone tower to capture enough power to charge the battery. It is further contemplated the human body may be used as an antenna; that is, the human body can pick up certain frequencies well (ankle bracelets, for example could be used to pick up power). The coil antenna is mentioned throughout the text. It is appreciated a coil is essentially a magnetic field coupling device. An electric field coupling antenna, such as a dipole, is also suitable and would be the preferred solution for far field powering of the implant. It is also appreciated that coupled coils (one on surface, one implanted) limit the amount of field passing deep into the body compared to a single coil on the surface of the skin transmitting power and may be employed in accordance with the present invention.

With the various embodiments of the present wireless monitoring system in mind, it is appreciated the present wireless implantable device contains a low power compact 64 channel digital EEG acquisition system readily adapted for use in conjunction with clinical scalp EEG acquisition. The EEG acquisition system of the present invention fully meets the current needs associated with clinical scalp EEG acquisition in terms of its capability in terms of channel count, A/D resolution, and sampling frequency. As such, the concepts underlying the processing of signals as utilized in the accordance with the present wireless monitoring system are applied as a very low cost replacement for a clinical EEG acquisition system. Further, due to its small size and low power consumption it also has additional applications, including portable use.

Figure 18:
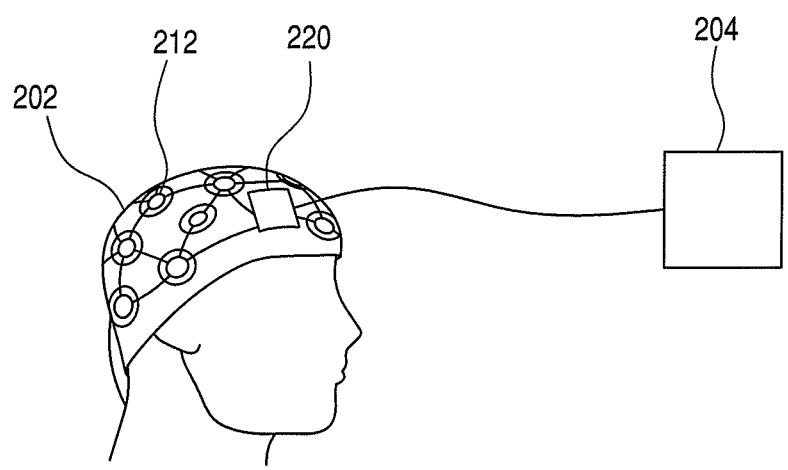
FIG. 18 is a schematic of an alternate embodiment employing a scalp EEG cap.
Figure 19:
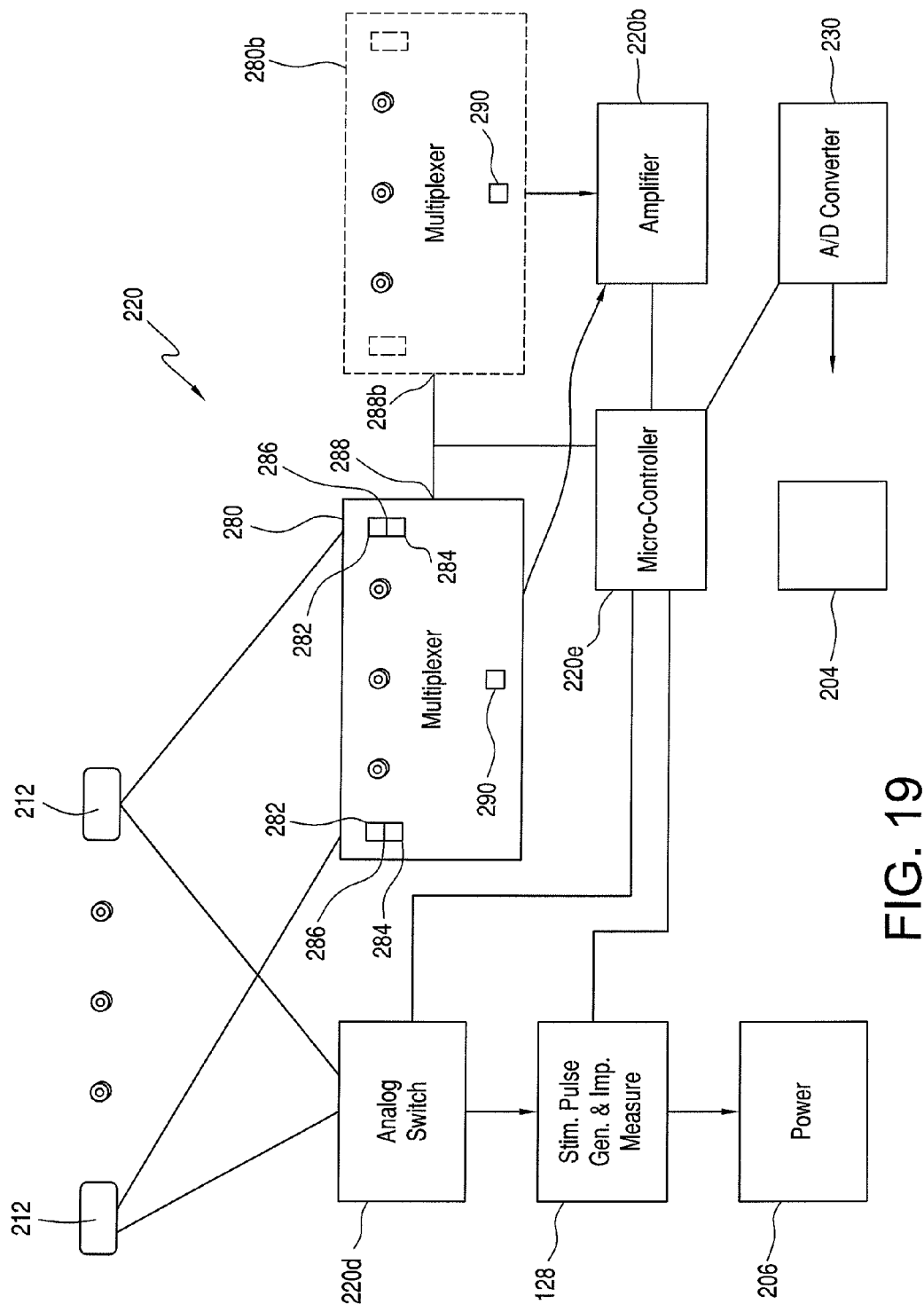
FIG. 19 is a schematic of the signal processing circuitry employed in the embodiment of the FIG. 18.

Referring now to FIGS. 18 to 19, a clinical scalp EEG system 200 applying the processing of signals as utilized in the accordance with the present wireless monitoring system is disclosed. In accordance with such a system, scalp EEG electrode placement of individual electrodes 212 or a traditional scalp electrode cap 202 with electrodes 212 is provided and adapted for conventional positioning about the scalp of the individual undergoing testing. It is appreciated that although it is easier to use scalp EEG electrodes when integrated with a cap, it is more common that the electrodes are individually attached to the scalp and less commonly attached with a scalp cap. Regardless, the concepts underlying the present invention may be applied in either situation, although the present invention is disclosed herein through the use of scalp electrode cap. The various electrodes 212 are directly connected to signal conditioning and digitizing circuitry, or signal processing circuitry 220 as used in the following disclosure, which is mounted upon the scalp electrode cap 202. The signal processing circuitry 220 is similar to that disclosed above with reference to FIGS. 13, 15, 16 and 17 and would be mounted upon the scalp electrode cap 202.

As such, the signal processing circuitry 220 employed in accordance with the clinical scalp EEG system 200 disclosed herein, is adapted for 64 EEG channels and 1 reference channel. The signal processing circuitry 220 employs dual multiplexers 280, 280a within the signal path of the signal processing circuitry 220. The signal processing circuitry 220 samples each electrode 212 at a rate that is at least twice the highest frequency of the electrode signal. Anti aliasing filtering at the input of each channel, that is, electrode 212 connected, to the multiplexer 280 is achieved by the provision of an array of series L (as ferrite beads) and shunt capacitors 282 at the input of each channel on the multiplexer 280. In addition to limiting the frequency content of the input signal to be measured, the provision of an array of series L and shunt capacitors 282 at the input of each channel to the multiplexer 280 also filters out unwanted noise and the RF field powering the circuit.

The multiplexers 280, 280b employed in accordance with a preferred embodiment of the present invention is effectively DC coupled. The circuit is AC coupled but the rapid switching of the multiplexers 280, 280b and electrodes 212 makes it able to measure instantaneous DC voltages. The multiplexers 280, 280b includes a low pass filter 284 at each channel input 286 and should be able to operate with an input potential of at least 100 millivolts above or below ground to accommodate the potentials measured within the human body. A resistor to ground is also provided at each channel input 286 to bleed off charge between measurement intervals.

As the largest number of channels commercially available on a multiplexer is 32 channels, the present signal processing circuitry employs parallel multiplexers 280, 280b. The address lines of the multiplexers 280, 280b are paralleled and the Enable pin 288, 288b is used to select specific multiplexers. The rapid switching of the channel inputs 286 of the multiplexer 280 produces a high frequency signal at the output 290 of the multiplexers 280, 280b. That high frequency signal at the output 290 of the multiplexers 280, 280b is modulated with the voltages of the electrodes 212 of the selected channels.

As with the prior embodiments, the signal processing circuitry 220 includes an amplifier 220b. In accordance with a preferred embodiment, the amplifier 220b is a high speed op amp that amplifies pulses modulated by the selected channels. The gain of the amplifier 220b is about 25 dB. The pulses for a 64 KHz system sampled at 1 KHz are 15.6 µsec in width. The amplifier 220b should have very low noise and respond with no overshoot or ringing. Ringing in the amplifier 220b can cause crosstalk into adjacent channels. A roll off capacitor is used in the feedback circuit to reduce the amplifier bandwidth for increased signal to noise ratio.

Only one amplifier 220b is needed for all the channels of the EEG system 200. The ability to amplify 64 channels of information with a single amplifier 220b achieves similar gain, offset and noise characteristics for all channels. Since the signals are high speed pulse signals, they are removed from low frequency noise such as Shot Noise and a small coupling capacitor can be used to couple the signal into the op amp.

The amplifier 220b is designed with additional circuitry capable of measuring DC voltages at the electrodes 212 of the scalp electrode cap 202. The DC level is converted to pulse amplitude by the switching of the multiplexer 280.

The amplified signals are digitally converted by an A/D converter 230. The A/D converter 230 is a high speed 16 bit converter. The reference voltage for the A/D converter 230 is generated through a low noise reference voltage diode which serves to isolate the converted signal from power supply noise. The A/D converter 230 also has capacitors on the power supply to reduce noise. The A/D converter 230, as well as the other operating components of the signal processing circuitry 220 is controlled by the micro-controller 220e. As with the prior embodiment, the micro-controller 220e is an 8-bit microcontroller.

The micro-controller 220e controls the A/D converter 230, the multiplexer(s) 280, 280b, and measures the power supply voltage. The micro-controller 220e receives commands and transmits to the various components of the signal processing circuitry 220. The micro-controller 220e is programmable on the circuit board of the signal processing circuitry 220. The micro-controller 220e is also capable of receiving commands that instruct which channels to measure and to set the sampling rate. If a particular set of channels have signals of interest, it is possible it measure them with higher time resolution to increase waveform fidelity. It is also possible to use extra multiplexer channels for various additional purposes as discussed above with regard to the previously discussed embodiments.

The data and control communication are preferably conducted over wires leading to EEG recording device 204. Each data frame transmitted by the signal processing circuitry 220, contains data for 64 channels, communication start and stop information and communication error detection information. When a frame is received by the main circuitry EEG recording device 204 a time-stamp is inserted into it. This time-stamp allows the EEG data stream to be synchronized with a video data stream, thus allowing the EEG and video streams to be viewed in a synchronized manner.

With the exception of the IR and RF circuitry found in the previously discussed embodiments, the specifics of the circuitry employed in accordance with the signal processing circuitry 220 is similar to that disclosed with reference to FIGS. 15, 16 and 17 in relation to the remote circuitry 120 of that embodiment.

As with the prior embodiments, the electrodes 212 are connected by an analog switch network 220d (as explained in detail with reference to FIG. 7). The analog switch network 220d creates connections between individual electrodes and functional circuitry 228 which provides tissue stimulation current and which enables remote circuitry 220 to measure electrode impedance (detailed in FIG. 7) under the control of the microcontroller 220e.

The scalp EEG cap 202 and signal processing circuitry 220 of the EEG system 200 described above may be configured for use in a battery powered 206, standalone, full channel count, wired, ambulatory EEG system 200 as shown with reference to FIG. 18. This would be a standalone EEG system 200 with the capability to record digital EEG data. The EEG recording device 204 could be carried in a pocket, worn on a belt, integrated within an EEG electrode cap, baseball cap or other cap. Regardless of the location of the EEG recording device 204 it would be directly wired to the A/D converter 230 for receipt of signals generated by the signal processing circuitry 220. Such a configuration would require the capability to store a few days of digital EEG data within the recording device, which is believed to be well within the capabilities of current technology. It is also appreciated, wireless re-charging of the battery and wireless data transfer when the unit is within range of a base station are possible.

Figure 20:
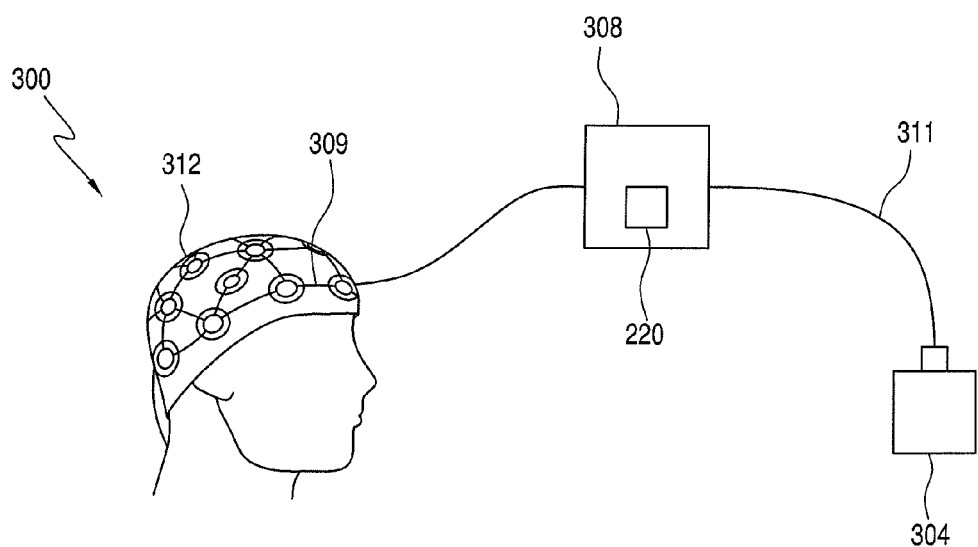
FIGS. 20 and 21 are schematics of an alternate embodiment employing a scalp EEG cap.

In accordance with an alternate embodiment as shown with reference to FIG. 20, the signal processing circuitry 220 described above may also be configured for use with a USB, battery, or mains powered digital EEG system 300. In accordance with such an embodiment, a headbox 308 is a connection point between scalp EEG electrodes 312 and the EEG recording device 304. The individual scalp EEG electrode wires 309 are brought to the headbox 308, where they are processed using the present signal processing circuitry 220 and the analog signals then proceed from the headbox 308 to the EEG recording device 304 in a single USB cable 311. In accordance with this embodiment, the present signal processing circuitry 220 is integrated within the EEG headbox 308, wherein the EEG signals are amplified and digitized in the headbox 308. The headbox 308 is then connected in a wired or wireless manner to the EEG recording device 304 in the form of a smartphone/tablet/notebook/laptop/desktop computer. The digital EEG would be communicated to this connected EEG recording device to be displayed and stored. It is appreciated that in a USB version the entire signal conditioning system would be powered over the USB cable 311 by the connected EEG recording device 304, and would transmit digital EEG over the USB cable 311 to it. In the battery or mains powered versions the EEG device would transmit digital EEG data in a wired or wireless manner to the connected computing device.

Figure 21:
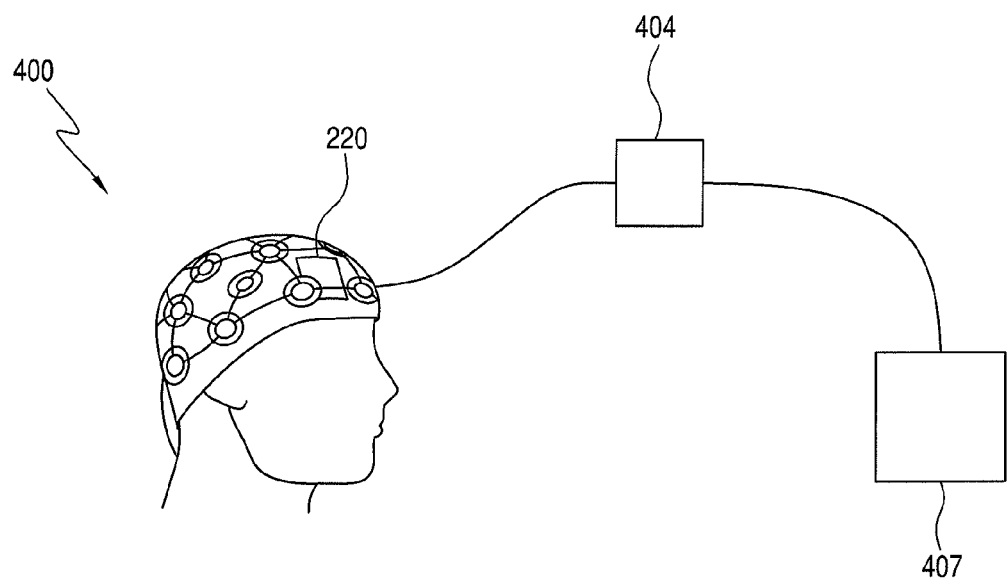

In accordance with yet another alternate embodiment as shown in FIG. 21, the signal processing circuitry 220 described above may also be configured for use with a battery or USB powered, full channel count, portable digital EEG acquisition system 400. This configuration is similar to the first configuration above but without the built-in capability to record EEG. The EEG recording device 404 is connected instead to a smartphone/tablet/notebook/laptop 407 to serve as a portable full capacity EEG system. In accordance with an alternate configuration, the use of a smartphone (or other devices) 407 can allow continuous transmission of the EEG or computed parameters of the EEG to allow true remote monitoring of a patient or subject. In the USB version the EEG device would be powered over the USB cable by the connected computing device, and would transmit digital EEG over the USB cable to it. In the battery powered version the EEG device could transmit digital EEG data in a wired or wireless manner to the connected computing device.

These configuration would provide for the possibility that the concepts underlying the processing of signals as utilized in the accordance with the present wireless monitoring system could be applied for field use, for example, in sports to test for concussion, during driving, flying and operating heavy machinery to check for drowsiness or distraction, or in the battlefield to check for brain injury. These concepts could also be used for ambulatory applications, for example, for ambulatory monitoring to record EEG for a few days, or the present wireless monitoring system may be employed in first responder applications to document patient mental status. They may also be used in emergency room applications to document and assess patient mental status, in intensive care unit/neurointensive care application as a bedside monitor to record EEG in ICU/NICU setting, in operating room applications to monitor depth of anesthesia, and in clinical EEG applications as a replacement for clinical EEG equipment, in low cost and other markets.

It is further appreciated the scalp EEG systems described above may be modified in various manner, for example, (1) Sample synchronously with 50/60 Hz to reduce artifact; (2) Include 50/60 Hz notch filter before the multiplexers; (3) Use magnetic shielding on the circuitry; and (4) Use electric shielding on the circuitry.

While the principles of this invention have been described in connection with specific embodiments, it should be understood clearly that these descriptions are made only by way of example and are not intended to limit the scope of the invention.

The invention claimed is:

1. A wireless system for brain monitoring/mapping of neurological-disorder patients, the system comprising:
   a plurality of electrodes each configured for surface abutment of brain tissue;
   main circuitry for placement outside a body of a patient and configured to transmit power at radio frequencies and send and receive data using infrared energy; and
   remote circuitry for subcutaneous implantation in a head of the patient, the remote circuitry being connected to the plurality of electrodes and including a multiplexer sampling signals from the plurality of electrodes, the multiplexer outputting electrode signals to an amplifier and A/D converter for transmission to the main circuitry, wherein the remote circuitry is configured to (a) receive transmitted power at radio frequencies from the main circuitry, (b) capture and digitize full-bandwidth EEG signals from each of the electrodes, and (c) send data to and receive data from the main circuitry using infrared energy, including sending the digitized full-bandwidth EEG signals from each of the electrodes.

2. The wireless neurological-disorder monitoring/mapping system of claim 1 wherein the remote circuitry includes a second multiplexer.

3. The wireless neurological-disorder monitoring/mapping system of claim 1, wherein the remote circuitry is configured to measure electrical impedance of each of the plurality of electrodes.

4. The wireless neurological-disorder monitoring/mapping system of claim 3 wherein the remote circuitry is configured to send the measurements of the electrical impedance to the main circuitry as digital signals.

5. The wireless neurological-disorder monitoring/mapping system of claim 1 wherein the radio frequencies are in a range of between 13.55 MHz and 13.57 MHz.

6. The wireless neurological-disorder monitoring/mapping system of claim 1 wherein the remote circuitry further includes a power storage capacitor, whereby the capacitor provides power when high current flow is required.

7. The wireless neurological-disorder monitoring/mapping system of claim 1 wherein the remote circuitry further includes a battery to augment the RF-supplied power.

8. The wireless neurological-disorder monitoring/mapping system of claim 7 wherein the battery is a solid-state lithium rechargeable battery.

9. The wireless neurological-disorder monitoring/mapping system of claim 8 wherein the remote circuitry further includes a power storage capacitor, whereby the capacitor provides power when high current flow is required.

10. The wireless neurological-disorder monitoring/mapping system of claim 1 further including a video camera and recording system to synchronously record the full-bandwidth EEG signals and video images of the patient.

11. The wireless neurological-disorder monitoring/mapping system of claim 1 wherein the remote circuitry is further configured to provide electrical energy to at least one of the plurality of electrodes to stimulate brain tissue.

12. The wireless neurological-disorder monitoring/mapping system of claim 11 wherein the remote circuitry is further configured to measure electrical impedance of each of the plurality of electrodes.

13. The wireless neurological-disorder monitoring/mapping system of claim 12 wherein the remote circuitry is further configured to send the measurements of the electrical impedance to the main circuitry as digital signals.

14. The wireless neurological-disorder monitoring/mapping system of claim 13 wherein the radio frequencies are in a range of between 13.55 MHz and 13.57 MHz.

15. The wireless neurological-disorder monitoring/mapping system of claim 1 wherein the multiplexer include an array of series L and shunt capacitors at each channel input.

16. The wireless neurological-disorder monitoring/mapping system of claim 1 wherein the multiplexer includes a low pass filter at each channel input.

17. The wireless neurological-disorder monitoring/mapping system of claim 1 wherein gain of the amplifier is about 25 dB.

18. A signal processing circuitry for brain monitoring/mapping of neurological-disorder patients, comprising:
   a plurality of electrodes;
   a multiplexer sampling signals from the plurality of electrodes, the multiplexer outputting electrode signals;
   an amplifier receiving electrode signals output by the multiplexer; and
   A/D converter receiving amplified signals from the amplifier for transmission to an EEG recording device.

19. The signal processing circuitry of claim 18 wherein the remote circuitry includes a second multiplexer.

20. The signal processing circuitry of claim 18 wherein the multiplexer include an array of series L and shunt capacitors at each channel input.

21. The signal processing circuitry of claim 18 wherein the multiplexer includes a low pass filter at each channel input.

22. The signal processing circuitry of claim 18 wherein gain of the amplifier is about 25 dB.

\* \* \* \* \*